US011623013B2

(12) United States Patent
Smith et al.

(10) Patent No.: US 11,623,013 B2
(45) Date of Patent: Apr. 11, 2023

(54) METHODS AND COMPOSITIONS FOR DEUTERATED BIOLOGICS

(71) Applicant: BRISTOL-MYERS SQUIBB COMPANY, Princeton, NJ (US)

(72) Inventors: Michael J. Smith, Somerset, NJ (US); Haiying Tang, Morganville, NJ (US); Paul E. Morin, Pennington, NJ (US); Harold J. Malone, Spring Lake, NJ (US); Luciano Mueller, Princeton, NJ (US)

(*) Notice: Subject to any disclaimer, the term of this patent is extended or adjusted under 35 U.S.C. 154(b) by 0 days.

(21) Appl. No.: 17/093,941

(22) Filed: Nov. 10, 2020

(65) Prior Publication Data

US 2021/0060184 A1    Mar. 4, 2021

Related U.S. Application Data

(62) Division of application No. 16/148,604, filed on Oct. 1, 2018, now abandoned.

(60) Provisional application No. 62/566,924, filed on Oct. 2, 2017.

(51) Int. Cl.
*A61K 49/18* (2006.01)
*A61K 47/68* (2017.01)
*A61K 49/12* (2006.01)

(52) U.S. Cl.
CPC ...... *A61K 49/1857* (2013.01); *A61K 47/6851* (2017.08); *A61K 49/126* (2013.01)

(58) Field of Classification Search
CPC ............ A61K 49/1857; A61K 47/6851; A61K 49/126
See application file for complete search history.

(56) References Cited

U.S. PATENT DOCUMENTS

2016/0176963 A1    6/2016    Maurer
2016/0176979 A1    6/2016    Magliery

FOREIGN PATENT DOCUMENTS

WO    2016086021 A1    6/2016

OTHER PUBLICATIONS

Pelham et al., Clinical trial: single- and multiple-dose pharmacokinetics of, 2008, 256, 28, Alimentary Pharmacology & Therapeutics.
Polymer Source Product Deuterated Poly (Ethylene Glycol) Dihydroxy Terminated, 2011, Polymer Source Product File Deuterated.
Swierczewska et al, What is the future of PEGylated therapies, 2015, 1, 20, Expert Opinion Emerge Drugs.
Thomas Gant, Deuterium in Drug Discovery: Leaving the Label in the Drug, 2014, 3595, 57, JMEDCHEM.
Turecek et al, PEGylation of Biopharmaceuticals: A Review of Chemistry and Nonclinical Safety Information of Approved Drugs, 2016, 461, 105, Journal of Pharmaceutical Sciences.
Zhang et al., Pegylation of Lysine Residues Improves the Proteolystic Stability of Fibronectin While Retaining Biological Activity, 2014, 1033_1043, 9, Biotechnol J.
De Feyter et al; Science Advances; "Deuterium metabolic imaging (DMI) for MRI-based 3D mapping of metabolism in vivo"; vol. 4; eaat 7314; pp. 1-11; 2018.

*Primary Examiner* — James W Rogers
(74) *Attorney, Agent, or Firm* — Gregory R. Bellomy

(57) ABSTRACT

Deuterated polymer-biomolecule conjugates and the synthesis and use of deuterated polymer-biomolecule conjugates for detecting the location of specific molecules, e.g., cell surface molecules, in a subject, and for imaging various processes within the body, for detecting the location of molecules associated with disease pathology, and for monitoring disease progression are disclosed.

18 Claims, 6 Drawing Sheets

Specification includes a Sequence Listing.

SEQUENCE LISTING

<160> NUMBER OF SEQ ID NOS: 9

<210> SEQ ID NO 1
<211> LENGTH: 94
<212> TYPE: PRT
<213> ORGANISM: Artificial Sequence
<220> FEATURE:
<223> OTHER INFORMATION: WT 10Fn3 Domain

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 94
<212> TYPE: PRT
<213> ORGANISM: Artificial Sequence
<220> FEATURE:
<223> OTHER INFORMATION: PDL-1 FBS (A02)

<400> SEQUENCE: 2

Val Ser Asp Val Pro Arg Asp Leu Glu Val Val Ala Ala Thr Pro Thr
1               5                   10                  15

Ser Leu Leu Ile Ser Trp Ser Tyr Asp Gly Pro Ile Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Asp Gln Lys Thr Ala Thr Ile Ser Gly Leu Lys Pro
    50                  55                  60

Gly Val Asp Tyr Thr Ile Thr Val Tyr Ala Val Arg Leu Glu Glu Ala
65                  70                  75                  80

His Tyr Asn Arg Glu Phe Pro Ile Ser Ile Asn Tyr Arg Thr
                85                  90

<210> SEQ ID NO 3
<211> LENGTH: 92
<212> TYPE: PRT
<213> ORGANISM: Artificial Sequence
<220> FEATURE:

<223> OTHER INFORMATION: PDL1-FBS (E01)

<400> SEQUENCE: 3

Val Ser Asp Val Pro Arg Asp Leu Glu Val Val Ala Ala Thr Pro Thr
1               5                   10                  15

Ser Leu Leu Ile Ser Trp Arg Ala Gln Leu Ser Pro Ser Phe Tyr Tyr
            20                  25                  30

Arg Ile Thr Tyr Gly Glu Thr Gly Gly Asn Ser Pro Val Gln Glu Phe
        35                  40                  45

Thr Val Pro Asn Asp Val Met Thr Ala Thr Ile Ser Gly Leu Lys Pro
    50                  55                  60

Gly Val Asp Tyr Thr Ile Thr Val Tyr Ala Val Thr Thr His Gly Val
65                  70                  75                  80

Tyr Phe Tyr Ser Pro Ile Ser Ile Asn Tyr Arg Thr
                85                  90

<210> SEQ ID NO 4
<211> LENGTH: 94
<212> TYPE: PRT
<213> ORGANISM: Artificial Sequence
<220> FEATURE:
<223> OTHER INFORMATION: PDL-1 FBS (ATI-964)

<400> SEQUENCE: 4

Val Ser Asp Val Pro Arg Asp Leu Glu Val Val Ala Ala Thr Pro Thr
1               5                   10                  15

Ser Leu Leu Ile Ser Trp Ser Tyr Asp Gly Ser Ile Glu Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Asp Gln Lys Thr Ala Thr Ile Ser Gly Leu Lys Pro
    50                  55                  60

Gly Val Asp Tyr Thr Ile Thr Val Tyr Ala Val Arg Leu Glu Glu Ala
65                  70                  75                  80

His Tyr Tyr Arg Glu Ser Pro Ile Ser Ile Asn Tyr Arg Thr
                85                  90

<210> SEQ ID NO 5
<211> LENGTH: 94
<212> TYPE: PRT
<213> ORGANISM: Artificial Sequence
<220> FEATURE:
<223> OTHER INFORMATION: PDL-1 FBS (ATI-965)

<400> SEQUENCE: 5

Val Ser Asp Val Pro Arg Asp Leu Glu Val Val Ala Ala Thr Pro Thr
1               5                   10                  15

Ser Leu Leu Ile Ser Trp Thr Ala Tyr Asp Ser Val Asp Lys Tyr Tyr
            20                  25                  30

Arg Ile Thr Tyr Gly Glu Thr Gly Gly Asn Ser Pro Val Gln Glu Phe
        35                  40                  45

Thr Val Gly Pro Arg His His Thr Ala Thr Ile Ser Gly Leu Lys Pro
    50                  55                  60

Gly Val Asp Tyr Thr Ile Thr Val Tyr Ala Val Tyr His Thr Glu Pro
65                  70                  75                  80

Gly Tyr His Ala His Met Pro Ile Ser Ile Asn Tyr Arg Thr
                85                  90

```
<210> SEQ ID NO 6
<211> LENGTH: 90
<212> TYPE: PRT
<213> ORGANISM: Artificial Sequence
<220> FEATURE:
<223> OTHER INFORMATION: PDL-1 FBS (ATI-966)

<400> SEQUENCE: 6

Val Ser Asp Val Pro Arg Asp Leu Glu Val Val Ala Ala Thr Pro Thr
1               5                   10                  15

Ser Leu Leu Ile Ser Trp His Arg Phe Ser Ser Ile Met Ala Tyr Tyr
            20                  25                  30

Arg Ile Thr Tyr Gly Glu Thr Gly Gly Asn Ser Pro Val Gln Glu Phe
        35                  40                  45

Thr Val Ala Gly Ser Val Asn Thr Ala Thr Ile Ser Gly Leu Lys Pro
    50                  55                  60

Gly Val Asp Tyr Thr Ile Thr Val Tyr Ala Val Thr Ile His Asn Val
65                  70                  75                  80

Ser Phe Pro Ile Ser Ile Asn Tyr Arg Thr
                85                  90

<210> SEQ ID NO 7
<211> LENGTH: 92
<212> TYPE: PRT
<213> ORGANISM: Artificial Sequence
<220> FEATURE:
<223> OTHER INFORMATION: PDL-1 FBS (ATI-967)

<400> SEQUENCE: 7

Val Ser Asp Val Pro Arg Asp Leu Glu Val Val Ala Ala Thr Pro Thr
1               5                   10                  15

Ser Leu Leu Ile Ser Trp Gln Gly Gln Leu Ser Pro Ser Phe Tyr Tyr
            20                  25                  30

Arg Ile Thr Tyr Gly Glu Thr Gly Gly Asn Ser Pro Val Gln Glu Phe
        35                  40                  45

Thr Val Pro Val Ala Ser Gly Thr Ala Thr Ile Ser Gly Leu Lys Pro
    50                  55                  60

Gly Val Asp Tyr Thr Ile Thr Val Tyr Ala Val Thr Ser His Gly Ile
65                  70                  75                  80

Tyr Phe Tyr Ala Pro Ile Ser Ile Asn Tyr Arg Thr
                85                  90

<210> SEQ ID NO 8
<211> LENGTH: 94
<212> TYPE: PRT
<213> ORGANISM: Artificial Sequence
<220> FEATURE:
<223> OTHER INFORMATION: PDL-1 FBS (ATI-968)

<400> SEQUENCE: 8

Val Ser Asp Val Pro Arg Asp Leu Glu Val Val Ala Ala Thr Pro Thr
1               5                   10                  15

Ser Leu Leu Ile Ser Trp Ile Ala Pro Phe Tyr Asn Val Ile Tyr Tyr
            20                  25                  30

Arg Ile Thr Tyr Gly Glu Thr Gly Gly Asn Ser Pro Val Gln Glu Phe
        35                  40                  45

Thr Val Pro Gly Thr Gly Tyr Thr Ala Thr Ile Ser Gly Leu Lys Pro
    50                  55                  60

Gly Val Asp Tyr Thr Ile Thr Val Tyr Ala Val Thr Asp Gly Ala Ser
65                  70                  75                  80
```

```
Ile Ala Ser Tyr Ala Phe Pro Ile Ser Ile Asn Tyr Arg Thr
                85                  90

<210> SEQ ID NO 9
<211> LENGTH: 96
<212> TYPE: PRT
<213> ORGANISM: Artificial Sequence
<220> FEATURE:
<223> OTHER INFORMATION: Glypican-3 FBS sequence

<400> SEQUENCE: 9

Val Ser Asp Val Pro Arg Asp Leu Glu Val Val Ala Ala Thr Pro Thr
1               5                   10                  15

Ser Leu Leu Ile Ser Trp Ser Asp Asp Tyr His Ala His Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Glu His Val Thr Ala Thr Ile Ser Gly Leu Lys Pro
        50                  55                  60

Gly Val Asp Tyr Thr Ile Thr Val Tyr Ala Val Thr Tyr Asp Gly Glu
65                  70                  75                  80

Lys Ala Ala Thr Asp Trp Ser Ile Ser Ile Asn Tyr Arg Thr Pro Cys
                85                  90                  95
```

METHODS AND COMPOSITIONS FOR DEUTERATED BIOLOGICS

CROSS-REFERENCE TO RELATED APPLICATIONS

This application is a divisional of U.S. application Ser. No. 16/148,604, filed Oct. 1, 2018, which claims the benefit under 35 U.S.C. § 119(e) of U.S. Provisional Application Ser. No. 62/566,924, filed Oct. 2, 2017; the disclosures of which are incorporated herein by reference.

SEQUENCE LISTING

Incorporated herein by reference in its entirety is a Sequence Listing named "180816_SEQT_12979USDIV_YC.txt" comprising SEQ ID NO:1 through SEQ ID NO:9, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Aug. 16, 2018, and is approximately 9 KB in size.

FIELD

The invention relates to conjugates containing deuterated polymers and a biomolecule that binds to a target, and the synthesis and use of deuterated-polymer-biomolecule conjugates for imaging various processes within the body, for detecting the location of molecules, e.g., biomarkers, such as those associated with disease pathology, and for monitoring disease progression.

BACKGROUND

There is a need for non-invasive, non-toxic and practical in vivo imaging methodologies to detect molecules, such as molecules that serve as biomarkers, in a subject. For example, there is a need for methodologies to provide whole body imaging, e.g., for detecting the location of PD-L1 positive cells in a subject having cancer.

SUMMARY OF THE INVENTION

Provided herein are agents for use in diagnosis and imaging, e.g., whole body imaging (imaging agents). The agents are molecules comprising deuterium atoms, which molecules can be detected via Nuclear Magnetic Resonance (NMR) and Magnetic Resonance Imaging (MRI).

In one aspect, provided is a conjugate comprising a deuterated polymer (D-polymer) linked to a biomolecule ("D-polymer-biomolecule conjugate"). For example, a D-polymer-biomolecule conjugate may comprise a deuterated polyethylene glycol moiety (D-PEG), linked to a biomolecule (e.g., protein). In certain embodiments, the deuterated D-polymer-biomolecule conjugate is water soluble. In certain embodiments, the deuterated D-polymer is water soluble.

Generally, the molecular weight of the D-polymer is such that it is sufficient for being detected by MRI when it is deuterium labeled, and is not significantly toxic when administered to a subject, e.g., doses are chosen so that the conjugate comprising the D-polymer does not form levels of vacuoles that are physiologically unacceptable.

In some embodiments, the D-polymer in the conjugate comprises deuterated polyethylene glycol (D-PEG) and/or deuterated poly(propylene glycol) (D-PPG). In some embodiments, the D-polymer in the conjugate has an average molecular weight of between about 2 and about 100 kDa, preferably between about 2 and about 50 kDa.

In some embodiments, the D-polymer in the conjugate is deuterated polyethylene glycol (D-PEG), or a pharmaceutically acceptable salt thereof. In some embodiments, the D-PEG comprises $[O(CR_2)_2]_n$, wherein R is deuterium (D) or hydrogen (H), and n is an integer having a value that provides a molecular weight of the D-PEG that is sufficient for being detected by MRI when deuterium labeled, and that is not significantly toxic when administered to a subject (e.g., it does not form levels of vacuoles that are physiologically unacceptable). In certain embodiments, n is an integer from about 10 to about 2500. In some embodiments, n is an integer from about 20 to about 1000. In some embodiments, n is an integer from about 30 to about 800. In one embodiment, n is an integer from about 30 to about 600 or from about 30 to about 150. In some embodiments, between about 50% and 100% of the R atoms in the D-PEG are deuterium. In some embodiments, at least about 70% of the R atoms in the D-PEG are deuterium. In some embodiments, at least about 90% of the R atoms are deuterium.

In some embodiments, the biomolecule in the conjugate is a peptide or protein. In some embodiments, the biomolecule in the conjugate comprises an antibody or antibody fragment. In some embodiments, the biomolecule in the conjugate comprises a fibronectin based scaffold (FBS).

In related embodiments, the protein portion of the D-polymer-biomolecule conjugate comprises a ligand which binds to a biological molecule, e.g., a biological molecule associated with a disease. In some embodiments, the disease is selected from the group consisting of solid cancers, hematopoietic cancers, hematological cancers, autoimmune disease, neurodegenerative disease, cardiovascular disease and pathogenic infections. In certain embodiments, the protein portion of the conjugate binds to a tumor-associated antigen. In certain embodiments, the protein portion of the conjugate binds to a protein present on a pathogenic organism, e.g., a virus, bacterium or fungus.

In some embodiments, the D-polymer-biomolecule conjugate comprises a D-polymer as described herein directly linked to biomolecule (e.g., protein). In some embodiments, the D-polymer-biomolecule conjugate comprises a D-polymer, a linker moiety, and a protein.

In certain embodiments, the D-polymer-biomolecule conjugate provided herein is in the form of a pharmaceutical composition.

Any known method for linking a polymer to a biomolecule may be used to link a D-polymer to a biomolecule. In certain aspects, provided are methods for preparing a deuterated-polymer-biomolecule conjugate, the method comprising the steps of reacting a D-polymer comprising a terminal amine with a biomolecule in the presence of transglutaminase to form an amide bond between an amino group of the D-polymer and a carboxamide group of a glutamine residue in the targeting moiety.

In a related aspect, provided herein is a method of obtaining an image of a D-polymer-biomolecule conjugate as provided herein, the method including the steps of (a) administering the D-polymer-biomolecule conjugate to a subject; and (b) imaging in vivo the distribution of the D-polymer-biomolecule conjugate by magnetic resonance imaging. In some embodiments, the imaged distribution of the D-polymer-biomolecule conjugate is indicative of the presence or absence of a biomarker or a disease. A biomarker may be a marker whose presence or absence at specific location(s) at specific times indicates whether a subject is responding or is likely to respond to a given therapy, e.g., a cancer therapy. For example, a biomarker may be PD-L1 or other immune-oncology related biomarker, such as LAG-3, GITR, Ox-40, and TIGIT.

In a related aspect, there is provided a method of determining the distribution of a deuterated molecule in a subject, the method comprising (a) orally administering the deuterated molecule to the subject and (b) imaging in vivo the distribution of the deuterated molecule by magnetic resonance imaging (MRI). In a preferred embodiment, the deuterated molecule is D-PEG.

In a related aspect, provided herein is a method of diagnosing the presence of a disease in a subject, the method including the steps of (a) administering to a subject in need thereof a D-polymer-biomolecule conjugate as provided herein which binds to a target molecule associated with the presence of the disease; and (b) obtaining an image of at least a portion of the subject to detect the presence or absence of the D-polymer-biomolecule conjugate; wherein the presence and location of the D-polymer-biomolecule conjugate above background is indicative of the presence and location of the disease.

In a related aspect, provided herein is a method of monitoring the progress of a disease in a subject, the method including the steps of (a) administering to a subject in need thereof a D-polymer-biomolecule conjugate as provided herein which binds to a target molecule associated with the presence of the disease at a first time point and obtaining an image of at least a portion of the subject to determine the amount of the diseased cells or tissue; and (b) administering to the subject the D-polymer-biomolecule conjugate at one or more subsequent time points and obtaining an image of at least a portion of the subject at each time point; wherein the dimension and location of the diseased cells or tissue at each time point is indicative of the progress of the disease.

In a related aspect, provided herein is a method of quantifying diseased cells or tissues or cells or tissues that are positive for a given marker in a subject, the method including the steps of (a) administering to a subject, e.g., a subject having diseased cells or tissues, a D-polymer-biomolecule conjugate as described herein which binds to a target molecule, e.g., a target molecule that is located with the diseased cells or tissues; and (b) detecting the amount of the D-polymer-biomolecule conjugate in the subject, wherein the level and distribution of the D-polymer-biomolecule conjugate in the subject or in the diseased cells or tissues is a quantitative measure of the diseased cells or tissues or given marker, respectively.

In a related aspect, provided herein is a method of screening for an agent for treating a disease including the steps of (a) contacting a cells expressing a target protein associated with the disease with a D-polymer-biomolecule conjugate as provided herein which binds to the target protein in the presence and absence of a candidate agent; and (b) imaging the cells in the presence and absence of the candidate agent using magnetic resonance imaging (MRI), wherein a decrease in the amount of D-polymer-biomolecule conjugate in the presence of the candidate agent is indicative of that the agent binds to the target protein.

In some embodiments of these methods, the disease is selected from the group consisting of solid cancers, hematopoietic cancers, hematological cancers, autoimmune disease, neurodegenerative disease, cardiovascular disease and pathogenic infection (e.g., viral, bacterial or fungal infections).

In some aspects, provided herein is a method of obtaining a quantitative image of tissues or cells expressing a target protein, the method including the steps of contacting the cells or tissue with a D-polymer-biomolecule conjugate as provided herein which binds to the target protein, and detecting or quantifying the tissue expressing the target protein using magnetic resonance imaging (MRI).

In some embodiments of the methods provided herein, the biomolecule in the conjugate comprises a protein. In some embodiments, the biomolecule is a ligand. In some embodiments, the biomolecule comprises an antibody or antibody fragment. In some embodiments, the biomolecule comprises a fibronectin based scaffold (FBS). In some embodiments, the D-polymer-biomolecule conjugate binds to a tumor-associated antigen or an immune-oncology associated marker. In still other embodiments, the D-polymer-biomolecule conjugate binds to a protein present on a pathogenic organism (e.g., a virus, bacterium or fungus).

Also provided herein are kits containing the D-polymer-biomolecule conjugate or reaction precursors for producing the D-polymer-biomolecule conjugate provided herein and instructions for using and/or producing the D-polymer-biomolecule conjugate.

Other features and advantages of the instant disclosure will be apparent from the following detailed description and examples, which should not be construed as limiting.

DETAILED DESCRIPTION

Figure 1:
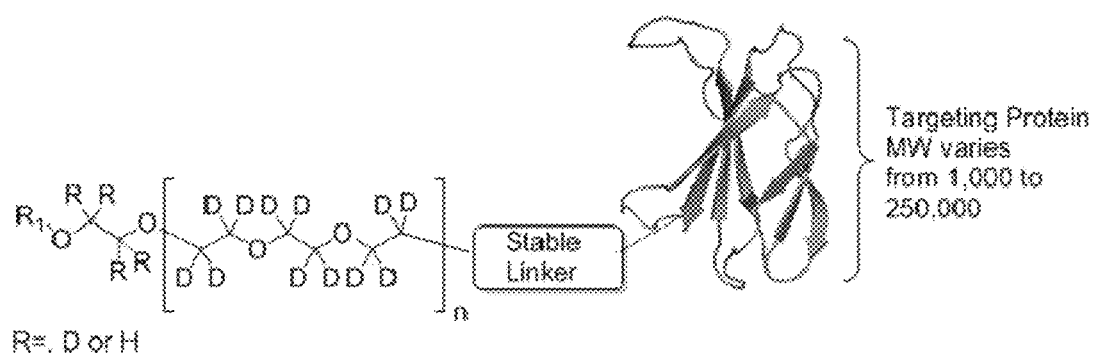
FIG. 1 is a schematic for a D-PEG-labeled protein conjugate provided herein.

Described herein are deuterium (D) labeled D-polymer (e.g., D-PEG) biomolecular conjugates, and the use of these conjugates as imaging agents to visualize the location of given molecules in a subject, such as for use as a prognostic, diagnostic or predictability biomarker, e.g., to confirm a response to a treatment or to predict the likelihood of response to a treatment, or to diagnose, localize, monitor and/or assess diseased cells and/or tissues, and related biological conditions. The methods may use deuterium NMR spectroscopy and MRI to detect the D-polymer-biomolecule conjugates.

Definitions

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of mass spectroscopy, NMR, MRI, HPLC, protein chemistry, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

As used herein, "about" means within plus or minus ten percent of a number. For example, "about 100" would refer to any number between 90 and 110.

The term "prosthetic group" refers to an organic molecule containing a detectable moiety that is capable of being linked to peptides or proteins.

As used herein, "target" as a general reference to a "biological target" refers to anything that can be targeted, e.g., a cell, tissue (e.g., cancer or tumor), a pathogenic microorganism (e.g., bacteria, virus, fungus, plant, prion, protozoa or portion thereof) or molecule thereon or molecule associated with a biological pathway, or a biological phenomenon, such as tissue inflammation, plaque formation, etc.

The term "targeting ligand", "targeting agent" or "targeting molecule" are used interchangeably to refer to a molecule, such as peptide, protein, glycoprotein, etc., that binds to another molecule. In certain embodiments, a targeting agent is bound to D-polymer in order to "target" a molecule associated with a particular cell, tissue, pathogen or biological pathway.

"Polypeptide" as used herein refers to any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In certain embodiments, polypeptides are purified (1) to greater than 95% by weight of polypeptide as determined by the Lowry method, or more than 99% by weight, (2) to a degree sufficient to obtain at least residues of N-terminal or internal amino acid sequence by use of a spinning cup sequenator, or (3) to homogeneity by SDS-PAGE under reducing or non-reducing condition using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

As used herein, a "$^{10}$Fn3 domain" or "$^{10}$Fn3 moiety" or "$^{10}$Fn3 molecule" refers to wild-type $^{10}$Fn3 and biologically active variants thereof, e.g., biologically active variants that specifically bind to a target, such as a target protein. A wild-type human $^{10}$Fn3 domain may comprise the amino acid sequence set forth in SEQ ID NO:1. Biologically active variants of a wild-type human $^{10}$Fn3 domain include $^{10}$Fn3 domains that comprise at least, at most or about 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to a $^{10}$Fn3 domain comprising SEQ ID NOs: 1.

An "Adnectin" or "Adx" or "adnectin" or "adx" refers to a human $^{10}$Fn3 molecule that has been modified (relative to the wild-type sequence) to bind specifically to a target.

A "region" of a $^{10}$Fn3 domain (or moiety or molecule) as used herein refers to either a loop (AB, BC, CD, DE, EF and FG), a β-strand (A, B, C, D, E, F and G), the N-terminus (corresponding to amino acid residues 1-7 of SEQ ID NO:1), or the C-terminus (corresponding to amino acid residues 93-94 of SEQ ID NO:1).

A "scaffold region" refers to any non-loop region of a human $^{10}$Fn3 domain. The scaffold region includes the A, B, C, D, E, F and G β-strands as well as the N-terminal region (amino acids corresponding to residues 1-7 of SEQ ID NO:1) and the C-terminal region (amino acids corresponding to residues 93-94 of SEQ ID NO:1).

The terms "specifically binds," "specific binding," "selective binding," and "selectively binds," as used interchangeably herein refers to an peptide or polypeptide that exhibits affinity for a biological target, but does not significantly bind (e.g., less than about 10% binding) to a other molecules as measured by a technique available in the art such as, but not limited to, Scatchard analysis and/or competitive binding assays (e.g., competition ELISA, BIACORE assay).

The term "preferentially binds" as used herein refers to the situation in which an peptide or protein binds a selected biological target at least about 20% greater than it binds a different biological target as measured by a technique available in the art such as, but not limited to, Scatchard analysis and/or competitive binding assays (e.g., competition ELISA, BIACORE assay).

The term "$K_D$," as used herein, is intended to refer to the dissociation equilibrium constant of an interaction between two molecules (e.g., D-polymer-biomolecule conjugate and target molecule) or the affinity of a D-polymer-polymer conjugate for a target molecule (e.g., a protein), as measured using a surface plasmon resonance assay or a cell binding assay. A "desired $K_D$," as used herein, refers to a $K_D$ of a D-polymer-biomolecule conjugate that is sufficient for the purposes contemplated. For example, a desired $K_D$ may refer to the $K_D$ of a D-polymer-biomolecule conjugate required to elicit a functional effect in an in vivo imaging assay or in vitro assay, e.g., NMR or MRI.

The term "$k_{ass}$" or "$k_a$", as used herein, is intended to refer to the association rate constant of two molecules, e.g., a D-polymer-biomolecule conjugate and its target.

The term "$k_{diss}$" or "$k_d$" used herein, is intended to refer to the dissociation rate constant for the dissociation of two molecules, e.g., a D-polymer-biomolecule conjugate and its target.

The term "$IC_{50}$", as used herein, refers to the concentration of a molecule, e.g., a D-polymer-biomolecule conjugate, that inhibits a response, either in an in vitro or an in vivo assay, to a level that is 50% of the maximal inhibitory response, i.e., halfway between the maximal inhibitory response and the untreated response.

The term "PK" is an acronym for "pharmacokinetic" and encompasses properties of a compound including, by way of example, absorption, distribution, metabolism, and elimination by a subject. A "PK modulation protein" or "PK moiety" as used herein refers to any protein, peptide, or moiety that affects the pharmacokinetic properties of a biologically active molecule when fused to or administered together with the biologically active molecule. Examples of a PK modulation protein or PK moiety include PEG, human serum albumin (HSA) binders (as disclosed in U.S. Publication Nos. 2005/0287153 and 2007/0003549, PCT Publication Nos. WO 2009/083804 and WO 2009/133208), human serum albumin and variants thereof, transferrin and variants thereof, Fc or Fc fragments and variants thereof, and sugars (e.g., sialic acid).

The "serum half-life" of a protein or compound can generally be defined as the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to a subject a suitable dose of the amino acid sequence or compound described herein; collecting blood samples or other samples from the subject at regular intervals; determining the level or concentration of the amino acid sequence or compound described herein in said blood sample; and calculating, from (a plot of) the data thus obtained, the time until the level or concentration of the amino acid sequence or compound described herein has been reduced by 50% compared to the initial level upon dosing. Reference is, for example, made to the standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

Half-life can be expressed using parameters such as the $t_{1/2}$-alpha, $t_{1/2}$-beta, HL_Lambda_z, and the area under the curve (AUC). In the present specification, an "increase in half-life" refers to an increase in any one of these parameters, any two of these parameters, any three of these parameters or all four of these parameters. An "increase in half-life" in particular refers to an increase in the $t_{1/2}$-beta, and/or HL_Lambda_z, either with or without an increase in the $t_{1/2}$-alpha and/or the AUC or both.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

The terms "diagnosis" or "detection" can be used interchangeably. Whereas diagnosis usually refers to defining a tissue's specific histological status, detection recognizes and locates a tissue, lesion or organism containing a particular detectable target.

The term "detectable" refers to the ability to detect a signal over the background signal. The term "detectable signal" as used herein in the context of imaging agents and diagnostics, is a signal derived from non-invasive imaging techniques such as, but not limited to, magnetic resonance imaging (MRI). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

A "detectably effective amount" of a composition comprising an imaging agent described herein is defined as an amount sufficient to yield an acceptable image using equipment that is available for clinical use. A detectably effective amount of an imaging agent provided herein may be administered in more than one injection. The detectably effective amount can vary according to factors such as the degree of susceptibility of the individual, the age, sex, and weight of the individual, idiosyncratic responses of the individual, and the like. Detectably effective amounts of imaging compositions can also vary according to instrument and methodologies used. Optimization of such factors is well within the level of skill in the art. In certain embodiments, a D-polymer-biomolecule conjugate, e.g., those described herein, provides a differentiation factor (i.e., specific signal to background signal) of 2 or more, e.g., 3, 4, 5 or more.

As used herein, "administering," as used in the context of imaging agents refers to the physical introduction of a composition comprising an imaging agent to a subject, using any of the various methods and delivery systems known to those skilled in the art. Preferred routes of administration for the imaging agents described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an imaging agent described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods. Preferably, a D-polymer, conjugated or otherwise, is administered intravenously, subcutaneously, or orally. More preferably, a conjugated D-polymer is administered intravenously.

The terms "co-administration" or the like, as used herein, are meant to encompass administration of the selected pharmaceutical agents to a single patient, and are intended to include regimens in which the agents are administered by the same or different route of administration or at the same or different time.

The terms "individual", "patient" and "subject" refer to any human or non-human animal, e.g., one that receives a composition comprising an imaging agent described herein.

As used herein, a labeled molecule is "purified" when the labeled molecule is partially or wholly separated from unlabeled molecules, so that the fraction of labeled molecules is enriched compared to the starting mixture. A "purified" labeled molecule may comprise a mixture of labeled and unlabeled molecules in almost any ratio, including but not limited to about 5:95; 10:90; 15:85; 20:80; 25:75; 30:70; 40:60; 50:50; 60:40; 70:30; 75:25; 80:20; 85:15; 90:10; 95:5; 97:3; 98:2; 99:1 or 100:0.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Various aspects described herein are described in further detail in the following subsections.

I. D-Polymer

In one aspect, provided herein is a D-polymer for use in a conjugation reaction. The D-polymer is soluble in an 100% aqueous medium, and there is no need for an organic phase to link the D-polymer to a peptide or protein molecule. This feature is particularly advantageous as many biologics (e.g., peptides or proteins) cannot withstand even small amounts of organic solvents, which can cause degradation and aggregation issues.

Provided herein are conjugates comprising a polymer, such as a water soluble polymer, that is labeled with deuterium (a "deuterium-polymer" or "D-polymer"). The polymer in a deuterium-polymer-biomolecule conjugate ("D-polymer-biomolecule conjugate") may be any polymer that can be labeled with deuterium and is detectable via MRI or other method for detecting deuterium, e.g., in a subject. In some embodiments, the deuterium atoms in the D-polymer are chemically equivalent, to, e.g., enhance sensitivity of detection.

The polymer chain may be a natural or synthetic polymer chain. In some embodiments, the polymer chain has a number average molecular weight (Mn) ranging up to about 10,000 kg/mol, for example from about 2-500 kg/mol, or from about 4-200 kg/mol. As used herein, Mn values may be determined by size exclusion chromatography coupled with a multi-angle laser light scattering (MALLS) detector and a refractive index detector to provide absolute molecular weights and size distributions.

Generally, the weight of the polymer will be such that it contains sufficient hydrogen atoms that can be substituted with deuterium, and is not significantly toxic to the subject to whom it is administered for imaging (e.g., whole body imaging) purposes. For example, the size of the polymer should not be such that the D-polymer-biomolecule conjugate has a half-life that is undesirable for the purpose (e.g., a half-life that is longer than 10 minutes, 30 minutes, 1 hour or a few hours). Also, preferably, the size or amount of the D-polymer or conjugate should be such that it does not creates an undesirable, e.g., toxic, level of vacuoles in the subject.

In some embodiments, the D-polymer in the conjugate is D-PEG. The term "PEG" is used broadly to encompass any polyethylene glycol molecule, without regard to size or to modification at an end of the PEG, and can be represented by the formula X—O(CH$_2$CH$_2$O)$_n$H, where n is 10 or more, e.g., 20 to 2500 and X is H or a terminal modification, e.g., a C$_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs.

Exemplary weight-average molecular weights for D-PEG in the conjugates provided herein include about 1,000 Daltons, about 2,000 Daltons, about 3,000 Daltons, about 4,000 Daltons, about 5,000 Daltons, about 6,000 Daltons, about 7,000 Daltons, about 8,000 Daltons, about 9,000 Daltons and about, 10,000 Daltons. In some embodiments, the PEG in the conjugate is between about 1 (preferably 2) and about 100 kDa. In some embodiments, the PEG in the conjugate is between about 2 and about 50 kDa. In some embodiments, the PEG in the conjugate is about 10, about 20, about 30, about 40, about 50, about 60, about 70, about 80, about 90 or about 100 kDa.

The D-PEG can be linear or branched. Branched versions of D-PEG having a total molecular weight of any of the foregoing can also be used. In some embodiments, the PEG has two branches. In other embodiments, the PEG has four branches. In one embodiment, the PEG is a bis-PEG (NOF Corporation, DE-200MA). In some embodiments, the PEG in the conjugate is linear.

In some embodiments, the D-PEG polymer comprises [O(CH$_2$)$_2$]$_n$, or a pharmaceutically acceptable salt thereof, wherein n is an integer from 10 to 2500. In some embodiments, n is an integer from 20 to 1000. In some embodiments, n is an integer from 30 to 800. In some embodiments, n is an integer from 30-600 or from 30 to 150.

In some embodiments, the structure of the D-PEG is D-PEG-XH, wherein X is O, S, or NH. In some embodiments, the D-PEG polymer is a maleimide-terminated D-PEG

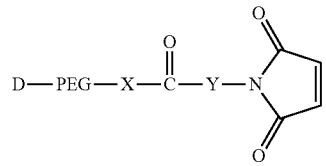

where Y can be —(CH$_2$)$_2$—, —C$_6$H$_4$—, or —C$_6$H$_{10}$—CH$_2$—.

In some embodiments, about 50% to 100% of the hydrogen molecules in the corresponding un-deuterated PEG molecule are replaced by deuterium. In some embodiments, at least about 50%, at least about 60%, at least about 70%, at least about 80%, at least about 85%, at least about 90%, at least about 95% or at least 98% of the hydrogens of the corresponding un-deuterated PEG have been replace by deuterium.

Suitable D-PEG molecules for use in the conjugates provided herein are available from Polymer Source Inc., Dorval (Montreal), Canada, in a variety of molecular weights (Mn) and having different terminal functional groups (OH, SH, NH$_2$) that can be used for conjugation to a targeting moiety, including, but not limited to HO—(CD$_2$CD$_2$O)$_n$—H (Product numbers P4837-dPEO, Mn 2.7; P4836-dPEO, Mn 3.5; and P4927-dPEO, Mn 4.8); CD$_3$CD$_2$O—(CD$_2$CD$_2$O)$_n$—H (Product number P3864A-dPEO, Mn 2.7); CH$_3$O—(CD$_2$CD$_2$O)$_n$—H (Product numbers P5381-dPEO-OCH$_3$, Mn 2.2; P11450-dPEO-OCH$_3$, Mn 5); CD$_3$O—(CD$_2$CD$_2$O)$_n$CD$_2$CD$_2$NH$_2$ (Product number P11448dPEG-OCH$_3$NH$_2$, Mn 5); and CH$_3$O—(CD$_2$CD$_2$O)$_n$CD$_2$CD$_2$SH (Product number P5381A-dPEOOCH$_3$SH, Mn 2) and CH$_3$CH$_2$O(CD$_2$CD$_2$)$_n$-H.

Any method for linking a D-PEG molecule to a biomolecule may be used, e.g., as described further herein. For example, one or more D-PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the D-PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

PEGylation of the biomolecule, e.g., protein, in the conjugate may be achieved by site-directed PEGylation, wherein a suitable reactive group is introduced into the protein to create a site where PEGylation preferentially occurs. In some embodiments, the protein is modified to introduce a cysteine residue at a desired position, permitting site-directed PEGylation on the cysteine. Mutations may be introduced into a protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework, based on which binding polypeptides are designed and evolved, has been solved (see Himanen et al., *Nature* 2001; 414:933-8) and thus the surface-exposed residues identified. PEGylation of cysteine residues may be carried out using, for example, PEG-maleimide, PEG-vinylsulfone, PEG-iodoacetamide, or PEG-orthopyridyl disulfide.

The D-PEG is typically activated with a suitable activating group appropriate for coupling to a desired site on the polypeptide. PEGylation methods are well-known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky (1995) *Advanced Drug Reviews* 16: 157-182.

II. Protein/Peptide Targeting Molecules

The D-polymer provided herein may be attached to virtually any targeting molecule (TM), so long as it contains a derivatizable group that may be modified without affecting the interaction between the targeting molecule and the in vivo biological target (e.g., protein, cell or tissue).

In some embodiments, the targeting molecule is a peptide or protein, including, but not limited to, antibodies, antibody fragments, fibronectin based molecules and ligands (e.g., hormones, growth factors, cytokines, chemokines, interleukins and angiogenic factors). In some embodiments, the targeting molecule will comprise one or more binding sites for a target, e.g., a target associated with a disease or condition, such as a tumor associated or autoimmune antigen, or immune-oncology related target, or a protein displayed by a pathogenic organism such as a virus, bacterium, fungus or protozoan.

In some embodiments, the D-polymer labeled peptides or protein may be selected to bind directly to a targeted cell, tissue, pathogenic organism or other target for imaging and/or detection. In other embodiments, D-polymer labeled protein or peptide may be selected to bind directly or indirectly to the in vivo target molecule. For example, a first protein or peptide may administered to the subject, followed by a second polymer-labeled molecule which binds to the first.

Peptides

Peptides having as few as two amino acid residues, preferably two to ten residues, may be used and may also be coupled to other moieties. The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

In some embodiments, peptides which may be used include ligands, peptide vaccines, and epitopes. The peptides used as targetable constructs are conveniently synthesized on an automated peptide synthesizer using a solid-phase support and standard techniques of repetitive orthogonal deprotection and coupling. N-terminal residues may be acetylated to increase serum stability. Such protecting groups will be known to the skilled artisan. See Greene and Wuts Protective Groups in Organic Synthesis, 1999 (John Wiley and Sons, N.Y.).

Antibodies

In certain embodiments, the targeting molecule used in the radiotracer composition described herein is an antibody. The term "antibody" as used to herein may include whole antibodies and any antigen binding fragments (i.e., "antigen-binding portions") or single chains thereof. By way of example "antibody" may refer to both naturally occurring and non-naturally occurring antibodies; monoclonal and polyclonal antibodies; chimeric and humanized antibodies; human and nonhuman antibodies; bispecific antibodies; wholly synthetic antibodies; dAbs and single chain antibodies and antigen binding fragments thereof.

The targeting molecules described herein may incorporate any antibody or fragment known in the art that has binding specificity for a target antigen associated with a disease state or condition. Antibodies useful as targeting molecules may be commercially obtained from a wide variety of sources (e.g., ATTC, Manassas, Va.), and/or have published variable region sequences which may be produced according to art recognized recombinant techniques. In some embodiments, exemplary antibodies for use in the present methods include an anti-CTLA-4 antibody, an anti-PD-1 antibody, an anti-PDL-1 antibody, an anti-OX40 (also known as CD134, TNFRSF4, ACT35 and/or TXGP1L) antibody, or an anti-LAG-3 antibody.

Antibodies used in the compositions and methods described herein can be produced using a variety of known techniques. Immunization protocols and techniques for isolation of immunized splenocytes are well established in the art. The production of monoclonal antibodies using the standard somatic cell hybridization technique described by Kohler and Milstein, Nature 256: 495 (1975), as well as viral or oncogenic transformation of B lymphocytes, phage display technique using libraries of human antibody genes are also routine. In addition, standard methodologies for the production of chimeric and humanized antibodies are readily available (see e.g., U.S. Pat. No. 4,816,567 to Cabilly et al.;

U.S. Pat. No. 5,225,539 to Winter, and U.S. Pat. Nos. 5,530,101; 5,585,089; 5,693,762 and 6,180,370 to Queen et al.).

In certain embodiments, the targeting molecule used in the conjugate is an antigen binding fragment. As used herein, the term "antigen-binding portion" of an antibody refers to one or more fragments of an antibody that retain the ability to specifically bind to an antigen. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

In certain embodiments, the antibody used is modified to modulate, e.g., decrease the half-life of the antibody or rapid clearance for use in the medical imaging methods described herein. Modifications such as I253A (Hornick et al. (2000) *J. Nucl. Med.* 41:355) and H435A/R I253A or H310A (Kim et al. (2000) *Eur. J. Immunol.* 29:2819) in Fc of human IgG1 can decrease FcRn binding. See also Kenanova et al. (2005) *Cancer Res.* 65:622. Other means to enhance clearance include formatting the antigen binding domains of the present invention as antibody fragments lacking the ability to bind FcRn, such as Fab fragments. Such modification can reduce the circulating half-life of an antibody from a couple of weeks to a matter of hours. Selective PEGylation of antibody fragments can then be used to fine-tune (increase in increments) the half-life of the antibody fragments if necessary. Chapman et al. (1999) *Nat. Biotechnol.* 17:780.

D-polymer-biomolecule conjugate compositions containing an antibody or antigen binding fragment thereof can be assayed for retention of binding specificity in vitro and/or in vivo. Methods for analyzing binding affinity, cross-reactivity, and binding kinetics of various antibody compositions include standard assays known in the art, for example, ELISA, Western Blotting, flow cytometry, and BIACORE® surface plasmon resonance (SPR) analysis using a BIACORE® 2000 SPR instrument (Biacore AB, Uppsala, Sweden).

Exemplary proteins for use in the D-polymer conjugates described herein include any known antibody or alternative scaffold protein, such as Adnectins, that specifically binds to a target, and does significantly cross-react with unrelated targets.

Fibronectin Based Protein (FBS)

In some embodiments, the targeting molecule used in the imaging compositions described herein is a FBS protein. Generally, FBS protein molecules have inherently rapid blood clearance rates, which can be advantageous for use with deuterium imaging technologies by minimizing the amount of time needed for background probe signals from non-relevant tissue. Rapid clearing probes allow high contrast images to be collected the same day the probe is injected, and very importantly, can also serve to reduce overall radiation exposure to the subject.

As used herein, a "fibronectin based scaffold" or "FBS" protein or moiety refers to proteins or moieties that are based on a fibronectin type III ("Fn3") repeat. Fn3 is a small (about 10 kDa) domain that has the structure of an immunoglobulin (Ig) fold (i.e., an Ig-like β-sandwich structure, consisting of seven β-strands and six loops). Fibronectin has 18 Fn3 repeats, and while the sequence homology between the repeats is low, they all share a high similarity in tertiary structure. Fn3 domains are also present in many proteins other than fibronectin, such as adhesion molecules, cell surface molecules, e.g., cytokine receptors, and carbohydrate binding domains. For reviews see Bork et al., *Proc. Natl. Acad. Sci. USA,* 89(19):8990-8994 (1992); Bork et al., *J. Mol. Biol.,* 242(4):309-320 (1994); Campbell et al., *Structure,* 2(5):333-337 (1994); Harpez et al., *J. Mol. Biol.,* 238(4):528-539 (1994)). The term "FBS" protein or moiety is intended to include scaffolds based on Fn3 domains from these other proteins (i.e., non fibronectin molecules).

An Fn3 domain is small, monomeric, soluble, and stable. It lacks disulfide bonds and, therefore, is stable under reducing conditions. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). There are at least 15 different Fn3 modules in human Fibronectin, and while the sequence homology between the modules is low, they all share a high similarity in tertiary structure.

The loops in Fn3 molecules are structurally similar to complementary determining regions (CDRs) of antibodies, and when altered, may be involved in binding of the Fn3 molecule to a target, e.g., a target protein. Other regions of Fn3 molecules, such as the beta or beta-like strands and N-terminal or C-terminal regions, when altered, may also be involved in binding to a target. Any or all of loops AB, BC, CD, DE, EF and FG may participate in binding to a target. Any of the beta or beta-like strands may be involved in binding to a target. Fn3 domains may also bind to a target through one or more loops and one or more beta or beta-like strands. Binding may also require the N-terminal or C-terminal regions. An FBS domain for use in a protein may comprise all loops, all beta or beta-like strands, or only a portion of them, wherein certain loops and/or beta or beta-like strands and/or N- or C-terminal regions are modified (or altered), provided that the FBS domain preferably binds specifically to a target. For example, an FBS domain may comprise 1, 2, 3, 4, 5 or 6 loops, 1, 2, 3, 4, 5, 6, 7, or 8 beta strands, and optionally an N-terminal and/or C-terminal region, wherein one or more loops, one or more beta strands, the N-terminal region and/or the C-terminal regions are modified relative to the wild-type FBS domain.

An example of FBS proteins that are based on human $^{10}$Fn3 domains are adnectins (Adnexus, a wholly owned subsidiary of Bristol-Myers Squibb). Adnectins are $^{10}$Fn3 molecules in which CDR-like loop regions, β-strands, N-terminal and/or C-terminal regions of a $^{10}$Fn3 domain has been modified to evolve a protein capable of binding to a compound of interest. For example, U.S. Pat. No. 7,115,396 describes $^{10}$Fn3 domain proteins wherein alterations to the BC, DE, and FG loops result in high affinity TNFα binders. U.S. Pat. No. 7,858,739 describes Fn3 domain proteins wherein alterations to the BC, DE, and FG loops result in high affinity VEGFR2 binders.

In certain embodiments, an FBS moiety is based on an Fn3 repeat other than the $10^{th}$ repeat of the type III domain of fibronectin, e.g., human fibronectin. For example, an FBS moiety may be similar to any of the other fibronectin type III repeats, e.g., the $1^{st}$, $2^{nd}$, $3^{rd}$, $4^{th}$, $5^{th}$, $6^{th}$, $7^{th}$, $8^{th}$, $9^{th}$, $11^{th}$, $12^{th}$, $13^{th}$, $14^{th}$, $15^{th}$, $16^{th}$, $17^{th}$, and $18^{th}$ Fn3 repeats. In yet other embodiments, an FBS moiety may be from a molecule other than fibronectin. Exemplary FBS moieties may be derived from tenascin, a protein that is composed of 15 Fn3 domains with similar sequence similarities to one another as found in fibronectin. These repeats are described, e.g., in Jacobs et al., *Protein Engineering, Design & Selection*, 25:107 (2012). Based on the homology of the repeats in the fibronectin molecule and those in the tenascin molecule, artificial molecules based on these homologies have been created. Proteins comprising a consensus amino acid sequence based on the homology of the domains in the fibronectin molecule are referred to as Fibcon and FibconB (WO 2010/093627 and Jacobs et al. (2012) supra.) and those based on the homology of the domains in the tenascin molecule are referred to as Tencon (WO 2010/051274, WO 2010/051310 and WO 2011/137319, which are specifically incorporated by reference herein). A Fibcon, FibconB or Tencon moiety, or target binding variants thereof, whether by itself or linked to a heterologous moiety may be fused as described herein. Fn3 domains from other proteins, e.g., cell surface hormone and cytokine receptors, chaperonins, and carbohydrate-binding domains, may be conjugated as described herein.

FBS proteins specific for any desired target molecule can be generated and tested using art recognized methods. Methods for testing the binding properties of FBS proteins are also well-known. For example, one way to rapidly make and test Fn3 domains with specific binding properties is the nucleic acid-protein fusion technology of Adnexus, a Bristol-Myers Squibb R&D Company. This disclosure utilizes the in vitro expression and tagging technology, termed 'PROfusion' which exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558, 6,261,804, 6,214,553, 6,281,344, 6,207,446, 6,518,018 and 6,818,418; Roberts et al., *Proc. Natl. Acad. Sci.*, 1997; 94:12297-12302; and Kurz et al., *Molecules*, 2000; 5:1259-64, all of which are herein incorporated by reference.

Exemplary FBS proteins or moieties included, but are not limited to those which bind to mesothelian, glypican, TL1A, CD8, myostatin, LPA1 receptors, TNF-alpha, VEGFR2, PCSK9, IL-23, EGFR or IGF1R and those which are described, e.g., in WO 2010/093627, WO 2011/130324, WO 2009/083804, WO 2009/133208, WO 02/04523, WO 2012/016245, WO 2009/023184, WO 2010/051310, WO 2011/020033, WO 2011/051333, WO 2011/051466, WO 2011/092233, WO 2011/100700, WO 2011/130324, WO 2011/130328, WO 2011/137319, WO 2010/051274, WO 2009/086116, WO 09/058379, WO2013/067029, WO2012/016245 and WO 2017/053619 (all of which are specifically incorporated by reference herein): any of the FBS proteins or moieties described in these publications may be used as described herein.

In some embodiments, the FBS protein binds to PDL-1. In some embodiments, the FBS protein comprises the amino acid sequence of any of SEQ ID NOs: 2-8 or a sequence set forth in WO2016086021. In certain embodiments, an imaging agent, e.g., comprising an FBS protein, is linked to a moiety that modulates, e.g., increases, its blood PK by small increments to enhance the imaging contrast or increase avidity of the D-polymer-biomolecule conjugate. In some embodiments, the clearance rate of the polypeptide in a mammal (e.g., mouse, rat, or human) is, or is increased by, greater than two-fold, greater than three-fold, greater than four-fold or greater than five-fold relative to the unmodified FBS protein. Moieties that slow clearance of a protein from the blood, herein referred to as "PK moieties", include polyoxyalkylene moieties (e.g., polyethylene glycol), sugars (e.g., sialic acid), and well-tolerated protein moieties (e.g., Fc and fragments and variants thereof, transferrin, or serum albumin). The FBS protein may also be fused to albumin or a fragment (portion) or variant of albumin as described in U.S. Publication No. 2007/0048282, or may be fused to one or more serum albumin binding FBS proteins, as described herein.

Other PK moieties that can be used in the invention include those described in Kontermann et al., (*Current Opinion in Biotechnology* 2011; 22:868-76), herein incorporated by reference. Such PK moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Protein Production

Proteins for use in the conjugates disclosed herein can also be produced using cell expression systems using host cells transformed with nucleic acids encoding the protein cultured in conventional nutrient media modified as appropriate for inducing promoters, selecting transformants, or amplifying the genes encoding the desired sequences. The host cells used to produce the proteins may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., *Meth. Enzymol.*, 58:44 (1979), Barnes et al., *Anal. Biochem.*, 102:255 (1980), U.S. Pat. Nos. 4,767,704; 4,657,866; 4,927,762; 4,560,655; or 5,122,469; PCT Publication Nos. WO 90/03430; WO 87/00195; or U.S. Pat. No. RE30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins can also be produced using cell-free translation systems. For such purposes, the nucleic acids encoding the protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins can also be produced by chemical synthesis (e.g., by the methods described in *Solid Phase Peptide Synthesis*, Second Edition, The Pierce Chemical Co., Rockford, Ill. (1984)). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis.

The purified protein is preferably at least 85% pure, more preferably at least 95% pure, and most preferably at least 98% or 99% pure. Regardless of the exact numerical value of the purity, the protein is sufficiently pure for use as a pharmaceutical product.

III. Conjugation of D-Polymers to-Biomolecules

D-polymers can be linked directly to a targeting moiety (TM), e.g., a protein or via a cross linking moiety. As used herein a linker is a molecule or group of atoms positioned between two moieties. Typically, linkers are bifunctional, i.e., the linker includes a functional group at each end, wherein the functional groups are used to couple the linker to the two moieties (e.g., D-PEG and targeting moiety). The two functional groups may be the same, i.e., a homobifunctional linker, or different, i.e., a heterobifunctional linker. In some embodiments the linker contains a maleimide group or derivative thereof. In some embodiments, the linker is a maleimide heterobifunctional reagent. In some embodiments, the linker is N-(p-Maleimideophenyl)isocyanate.

In some embodiments, the D-polymer-biomolecule conjugates have the following structure:

wherein the conjugate may comprise a D-polymer that is D-PEG or a D-polymer other than D-PEG.

In some embodiments, the D-polymer-biomolecule conjugates have the following structure:

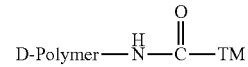

wherein TM is a targeting moiety, e.g., a protein.

In some embodiments, the D-polymer-biomolecule conjugates have the following structure:

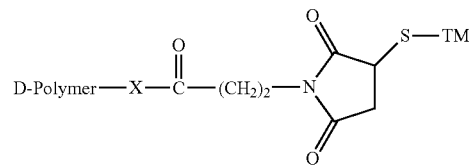

wherein X is O or NH.

In some embodiments, the D-polymer-biomolecule conjugates have the following structure:

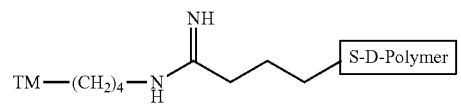

In some embodiments, the D-Polymer-biomolecule conjugates have the following structure:

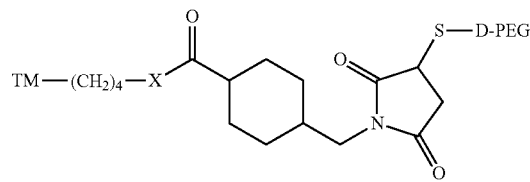

wherein X is NH or O, and wherein the D-PEG can also be a D-Polymer other than PEG.

In some embodiments, the D-Polymer-biomolecule conjugates have the following structure:

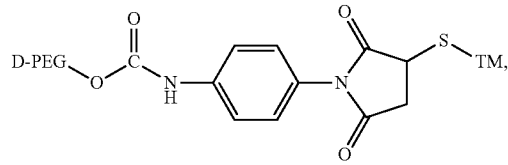

wherein the D-PEG can also be a D-Polymer other than PEG.

In some embodiments, the TM is a protein which is first modified to incorporate a cysteine for attaching the D-polymer. In some embodiments, $P_mX_n$ linked to the C-terminus of the protein contains a cysteine. For example, the first amino acid after the proline may be a cysteine, and the cysteine may be the last amino acid in the molecule or the cysteine may be followed by one or more amino acids. The presence of a cysteine permits the conjugation of heterologous moieties such as the D-polymer to the protein. Exemplary $P_mX_n$ moieties comprising a cysteine include: $P_mCX_n$, wherein C is a cysteine, each X is independently any amino acid, m is an integer that is at least 1 and n is 0 or an integer that is at least 1. In some embodiments, m may be 1, 2, 3 or more. For example, m may be 1-3 or m may be 1-2. "n" may be 0, 1, 2, 3 or more, e.g., n may be 1-3 or 1-2. Other exemplary PmXn moieties include two cysteines, for example, $PmCXn_1CXn_2$, wherein each X is independently any amino acid, n1 and $n_2$ are independently 0 or an integer that is at least 1. For example, $n_1$ may be 1, 2, 3, 4 or 5 and $n_2$ may be 1, 2, 3, 4 or 5. Exemplary PmXn moieties are disclosed in WO 2017/053619 (incorporated herein by reference).

In certain embodiments, the PmXn moiety is selected from the group consisting of PC, PPC and PCC. In another embodiment, the PmXn moiety is $PmCXn_1CXn_2$. In certain embodiments, $PmCXn_1CXn_2$ is selected from the group consisting of PCPPPC and PCPPPPPC.

In certain embodiments, the D-PEG polymer polymer can be bound, e.g., covalently linked, e.g., using maleimide chemistry, to a cysteine of a PmXn moiety on the protein moiety, wherein at least one X is a cysteine. Ligation to a cysteine can be performed as known in the art using maleimide chemistry (e.g., Imperiali, B. et al., *Protein Engineering: Nucleic Acids and Molecular Biology*, Vol. 22, pp. 65-96, Gross, H. J., ed. (2009)). For attaching a linker to a cysteine on a protein, the linker may, e.g., comprise a maleinimido moiety, which moiety then reacts with the cysteine to form a covalent bond. In certain embodiments, the amino acids surrounding the cysteine are optimized to facilitate the chemical reaction. For example, a cysteine may be surrounded by negatively charged amino acid for a faster reaction relative to a cysteine that is surrounded by a stretch of positively charged amino acids (EP 1074563). Linkage of a drug moiety to a cysteine on a protein moiety is a site specific linkage. Conventional separation and purification techniques known in the art can be used to purify D-polymer-biomolecule conjugates, such as size exclusion (e.g., gel filtration) and ion exchange chromatography. Products may also be separated using SDS-PAGE. Products that may be separated include mono-, di-, tri-, poly- and un-conjugated biomolecules, as well as free D-polymer. The percentage of mono-D-polymer-biomolecule conjugates can be controlled by pooling broader fractions around the elution peak to increase the percentage of mono-D-polymer-biomolecule conjugates in the composition. About 90% mono-D-polymer-biomolecule conjugates represent a good balance of yield and activity.

IV Targets

Exemplary in vivo target molecules which bind the D-polymer-biomolecule conjugates described herein are those associated with various diseases or conditions, such as a malignant disease, a cardiovascular disease, an infectious disease, an inflammatory disease, an autoimmune disease, or a neurological disease.

Provided herein are D-polymer-biomolecule conjugates (e.g., D-polymer labeled imaging agents) wherein the biomolecule binds specifically to a target, such as a protein on the surface of human cells. In certain embodiments, the biomolecule is a peptide; an antibody, or antigen binding portion thereof or a variant of an antibody; an alternative scaffold, such as an Fn3 (e.g., a human Fn3) domain, such as an FBS, e.g., a human $^{10}$Fn3 domain. In certain embodiments, the biomolecule binds to a cell surface molecule, e.g., a cell surface molecule on a tumor cell or a cell in the tumor, e.g., a tumor infiltrating lymphocyte that is located in the tumor. In certain embodiments, the moiety binds to a cell surface molecule on an immune cell, e.g., a T cell (e.g., a Treg cell), a Teff cell, a B cell, a macrophage, a dendritic cell, an NK cell or a Langerhans cell.

In certain embodiments, a D-polymer-biomolecule conjugate comprises a moiety that binds specifically to an immuno-oncology target (receptor or ligand), such as a co-stimulatory receptor on an immune cell (e.g., T cell or NK cell) or an inhibitor on an immune cell (e.g., a T cell or NK cell), which targets modulate immune responses. In one embodiment, the moiety binds to one of the following targets or ligand or receptor thereof: an immunoglobulin super family (IgSF) member; a member of the B7 family, which includes B7-1, B7-2, B7-H1 (PD-L1), B7-DC (PD-L2), B7-H2 (ICOS-L), B7-H3, B7-H4, B7-H5 (VISTA), and B7-H6; a member of the TNF receptor superfamily or its ligand, e.g., CD40, CD40L, OX-40, OX-40L, CD70, CD27L, CD30, CD30L, 4-1BBL, CD137, GITR, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR (see, e.g., Tansey (2009) Drug Discovery Today 00:1); a protein that inhibits an immune cell (e.g., immune checkpoint inhibitors), such as CTLA-4, PD-1, PD-L1, PD-L2, and LAG-3, TIM-3, Galectin 9, CEACAM-1, BTLA, CD69, Galectin-1, TIGIT, CD113, GPR56, VISTA, 2B4, CD48, GARP, CD73, PD1H, LAIR1, TIM-1, TIM-4, CD39; a protein that stimulates an immune response, such as B7-1, B7-2, CD28, 4-1BB (CD137), 4-1BBL, GITR, GITRL, ICOS, ICOS-L, OX40, OX40L, CD70, CD27, CD40, DR3 and CD28H; any of the following cell surface molecules: KIR, cytokine or interleukin receptors, IL-6, IL-10, TGF-ß, VEGF, CSF-1R, CD25 and IDO.

In some embodiments, the D-polymer-biomolecule conjugate binds to an antigen or receptor of a pathogen, including but not limited to fungi, viruses, parasites and bacteria. Examples of pathogenic viruses detectable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus. Examples of bacteria and fungi include, *Streptococcus agalactiae, Legionella pneumophilia, Streptococcus pyogenes, Escherichia coli, Neisseria gonorrhoeae, Neisseria meningitidis*, Pneumococcus, Hemophilis influenzae B, *Treponema pallidum*, Lyme disease spirochetes, *Pseudomonas aeruginosa*, *Mycobacterium leprae*, *Brucella abortus*, *Mycobacterium tuberculosis* and *Chlostridium tetani*.

Some examples of pathogenic bacteria causing infections detectable by methods described herein include *Chlamydia*, rickettsial bacteria, mycobacteria, staphylococci, streptococci, pneumonococci, meningococci and gonococci, *Klebsiella*, *Proteus*, *Serratia*, *Pseudomonas*, *Legionella*, diphtheria, *Salmonella*, bacilli, cholera, tetanus, botulism, anthrax, plague, leptospirosis, and Lyme disease bacteria.

Some examples of pathogenic fungi causing infections detectable by methods described herein include *Candida* (*albicans*, *krusei*, *glabrata*, *tropicalis*, etc.), *Cryptococcus neoformans*, *Aspergillus* (*fumigatus*, *niger*, etc.), Genus *Mucorales* (*mucor*, *absidia*, *rhizopus*), *Sporothrix schenkii*, *Blastomyces dermatitidis*, *Paracoccidioides brasiliensis*, *Coccidioides immitis* and *Histoplasma capsulatum*.

Some examples of pathogenic parasites causing infections detectable by methods described herein include *Entamoeba histolytica*, *Balantidium coli*, *Naegleriafowleri*, *Acanthamoeba* sp., *Giardia lambia*, *Cryptosporidium* sp., *Pneumocystis carinii*, *Plasmodium vivax*, *Babesia microti*, *Trypanosoma brucei*, *Trypanosoma cruzi*, *Leishmania donovani*, *Toxoplasma gondii*, and *Nippostrongylus brasiliensis*.

V. Biophysical and Biochemical Characterization

Binding of the D-polymer-biomolecule conjugates described herein to a molecule may be assessed in terms of equilibrium constants (e.g., dissociation, $K_D$) and in terms of kinetic constants (e.g., on-rate constant, $k_{on}$ and off-rate constant, $k_{off}$). A D-polymer-biomolecule conjugate will generally bind to a target with a $K_D$ of less than 500 nM, 100 nM, 10 nM, 1 nM, 500 pM, 200 pM, or 100 pM, although higher $K_D$ values may be tolerated where the $k_{off}$ is sufficiently low or the $k_{on}$, is sufficiently high.

Exemplary assays for determining the binding affinity of a D-polymer-biomolecule conjugate include, but are not limited to, solution phase methods such as the kinetic exclusion assay (KinExA) (Blake et al. *JBC* 1996; 271: 27677-85; Drake et al., *Anal Biochem* 2004; 328:3543), surface plasmon resonance (SPR) with the Biacore system (Uppsala, Sweden) (Welford et al., *Opt. Quant. Elect* 1991; 23:1; Morton and Myszka, *Methods in Enzymology* 1998; 295:268) and homogeneous time resolved fluorescence (HTRF) assays (Newton et al., *J. Biomol Screen* 2008; 13:674-82; Patel et al., *Assay Drug Technol* 2008; 6:55-68).

In certain embodiments, biomolecular interactions can be monitored in real time with the Biacore system, which uses SPR to detect changes in the resonance angle of light at the surface of a thin gold film on a glass support due to changes in the refractive index of the surface up to 300 nm away. Biacore analysis generates association rate constants, dissociation rate constants, equilibrium dissociation constants, and affinity constants. Binding affinity is obtained by assessing the association and dissociation rate constants using a Biacore surface plasmon resonance system (Biacore, Inc.). A-biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$ and $R_{max}$ (maximal response at saturation). Equilibrium dissociation constants for binding, $K_D$'s are calculated from SPR measurements as $k_{off}/k_{on}$.

In some embodiments, the D-polymer-biomolecule conjugates described herein exhibit a $K_D$ in the SPR affinity assay of 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, 10 nM or less, 5 nM or less, or 1 nM or less.

It should be understood that the assays described herein above are exemplary, and that any method known in the art for determining the binding affinity between a D-polymer-biomolecule conjugate and a target (e.g., fluorescence based-transfer (FRET), enzyme-linked immunosorbent assay, and competitive binding assays (e.g., radioimmunoassays)) can be used to assess the binding affinities of the D-polymer-biomolecule conjugate described herein.

VI. Pharmaceutical Compositions

Further provided are compositions, e.g., a pharmaceutical compositions, containing one or a combination of D-polymer biomolecule conjugates (e.g., D-PEG-FBS conjugates), described herein, formulated together with a pharmaceutically acceptable carrier. Such compositions may include one or a combination of (e.g., two or more different) agents described herein. For example, a pharmaceutical composition described herein can comprise a combination D-polymer biomolecule conjugates. Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, a D-polymer-biomolecule conjugate may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzyl ethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the D-polymer-biomolecule conjugate in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of D-polymer-biomolecule conjugate which can be combined with a carrier material to produce a single dosage form will vary depending upon the subject being treated, and the particular mode of administration. The amount of D-polymer-biomolecule conjugate which can be combined with a carrier material to produce a single dosage form will generally be that amount of the composition which produces a detectable effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

VII. Administration

The D-polymer-biomolecule conjugates described herein are useful in a variety of in vivo imaging applications (e.g., for tissue or whole body imaging). In certain embodiments, the D-polymer-biomolecule conjugate can be used to image target-positive cells or tissues, e.g., target expressing tumors. For example, the D-polymer-biomolecule conjugate is administered to a subject in an amount sufficient to uptake the D-polymer-biomolecule conjugate into the tissue of interest. The subject is then imaged using an imaging system such as MRI for an amount of time appropriate for the deuterium content of the agent to be detectable. The D-polymer-biomolecule conjugate bound to cells or tissues expressing the targeting agent is then detected by the imaging system.

In certain embodiments, administration occurs in an amount of a D-polymer-biomolecule conjugate of between about 0.005 µg/kg of body weight to about 50 µg/kg of body weight per day, usually between 0.02 µg/kg of body weight to about 3 µg/kg of body weight. A particular analytical dosage for the instant composition includes from about 0.5 µg to about 100 µg of a D-polymer-biomolecule conjugate. The dosage will usually be from about 1 µg to about 50 µg of a D-polymer-biomolecule conjugate.

Dosage regimens are adjusted to provide the optimum detectable amount for obtaining a clear image of the tissue or cells which uptake the D-polymer-biomolecule conjugate. It is especially advantageous to formulate parenteral compositions in dosage unit form for ease of administration and uniformity of dosage. Dosage unit form as used herein refers to physically discrete units suited as unitary dosages for the subjects to which the D-polymer-biomolecule conjugate is to be administered. The specification for the dosage unit forms described herein are dictated by and directly dependent on (a) the unique characteristics of the targeting portion of the D-polymer-biomolecule conjugate; (b) the tissue or cells to be targeted; (c) the limitations inherent in the imaging technology used.

For administration of the a D-polymer-biomolecule conjugate, the dosage used will depend upon the disease type, targeting compound used, the age, physical condition, and gender of the subject, the degree of the disease, the site to be examined, and others. In particular, sufficient care has to be taken about exposure doses to a subject. in some embodiments, a saturating dose of a D-polymer-biomolecule conjugate is administered to the patient.

In other embodiments, an effective amount of D-polymer-biomolecule conjugate will be the amount of compound sufficient to be visible by MRI or other deuterium detecting method in the subject.

Actual dosage levels of the active ingredients in the pharmaceutical compositions described herein may be varied so as to obtain an amount of the active ingredient which is effective to achieve the desired uptake of the D-biomolecule conjugate in the cells or tissues of a particular patient, composition, and mode of administration, without being toxic to the patient. It will be understood, however, that the total daily usage of the D-polymer-biomolecule conjugate of the present disclosure will be decided by the attending physician or other attending professional within the scope of sound medical judgment. The specific effective dose level for any particular subject will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; other drugs, compounds and/or materials used in combination with the particular compositions employed, the age, sex, weight, condition, general health and prior medical history of the patient being treated, and like factors well known in the medical arts. In certain embodiments, the amount of D-polymer-biomolecule conjugate administered into a human subject required for imaging will be determined by the prescribing physician.

A composition described herein can be administered via one or more routes of administration using one or more of a variety of methods known in the art. As will be appreciated by the skilled artisan, the route and/or mode of administration will vary depending upon the desired results. Preferred routes of administration for D-polymer-biomolecule conjugates described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In certain embodiments, the D-polymer-biomolecule conjugate is administered intravenously.

Alternatively, a D-polymer-biomolecule conjugate described herein can be administered via a non-parenteral route, such as a topical, epidermal or mucosal route of administration, for example, intranasally, orally, vaginally, rectally, sublingually or topically.

In certain embodiments, the D-polymer-biomolecule conjugate described herein can be formulated to ensure proper distribution in vivo. For example, the blood-brain barrier (BBB) excludes many highly hydrophilic compounds. Agents may cross the BBB by formulating them, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994).

VIII. Imaging Methods

Methods of imaging using D-polymer-biomolecule conjugate as targeting agents are provided herein. The D-polymer-biomolecule conjugate can be used with currently available MRI technology for use in exploratory and diagnostic imaging applications in vitro and in vivo. Imaging techniques and equipment for deuterium imaging by MRI scanning are well known in the art (see, e.g., Laracombe et al., Cancer Res. 50:363-369, 1990; Eskey et al., Cancer Res. 52:6010-6019, 1992; Obata et al., MRM 38:569-572, 1995; Furruya et al., Ann. Nucl. Med. 11:281-284, 1997) and any such known MRI imaging technique or apparatus may be utilized.

For example, after administration, the conjugates selectively accumulate to the region of interest in the subject (e.g., a region for which imaging is desired), and the resulting NMR signals emitted from the region of interest are detected. Imaging of the region of interest can be performed using any MM methods for acquisition of one or more images at particular time intervals after introducing the imaging agent to the subject and/or using any MRI scanning equipment. Modeling of the time dependence and its relationship to the obtained NMR signal may be employed for monitoring and quantitative evaluation of the spatial distribution of cells and tissues which bind the protein in the D-polymer-biomolecule conjugate (e.g., tumors), and are useful the detection of molecule of interest. The methods also provide a means for objectively mapping the total volume and distribution of the D-polymer-biomolecule conjugate, including areas of high and low capacity. Such mapping is particularly useful for detecting changes over time, for example, to monitor disease progression and/or response to drug therapy, radiation or chemotherapy.

IX. Uses

In vivo applications of the imaging methods provided herein include disease diagnosis, monitoring of disease progression, prognosis, determining likelihood of a subject to respond to a treatment, determining eligibility to a treatment, monitoring of clinical response to therapy, clinical evaluation and dose selection of therapeutic compounds, preclinical studies of potential drug candidates in animal models, and the study of regional distribution and concentration of target molecules in tissues and organs. In vitro applications include screening of drug candidates in cell assays (e.g., competition assays, affinity assays, etc.)

In some embodiments, the D-polymer-biomolecule conjugate can be used to determine the relationship between level of tissue occupancy by candidate therapeutic compounds and clinical efficacy in patients; to determine dose selection for clinical trials of drug candidates prior to initiation of long term clinical studies; and to compare potencies of different drug candidates.

In some embodiments, the D-polymer-biomolecule conjugate is used in a method for in in vivo imaging normal or diseased tissues and/or organs (e.g., lungs, heart, kidneys, liver, and skin). For example, the D-polymer-biomolecule conjugate is administered to a subject in an amount effective to result in uptake of the D-polymer-biomolecule conjugate into the cells or tissue of interest. The subject is then introduced to an appropriate imaging system (e.g., MRI system) for a sufficient amount of time to allow detection of the D-polymer-biomolecule conjugate. The location of the detected signal from the D-polymer-biomolecule conjugate can be correlated with the location of the cells or tissue of interest. In some embodiments, the dimensions of the location can be determined as well. In vivo imaging is described herein.

Accordingly, in certain aspects, provided is a method of obtaining an image of an D-polymer-biomolecule conjugate, the method comprising administering the D-polymer-biomolecule conjugate to a subject, and imaging in vivo the distribution of the D-polymer-biomolecule conjugate by MRI. The imaged distribution may be indicative of the location of the biomolecule and/or the target molecules to which the biomolecule binds.

In certain embodiments, a method is provided for determining the presence and/or quantity of a biomarker, e.g., a prognostic or predictive biomarker, in a subject, and based on the results, a subject is treated or not or has its treatment stopped or amended.

In certain aspects, provided is a method of diagnosing the presence of a disease in a subject, the method comprising administering to a subject in need thereof a D-polymer-biomolecule conjugate which binds to a target molecule associated with the presence of the disease, and obtaining a radio-image of at least a portion of the subject to detect the presence or absence of the D-polymer-biomolecule conjugate.

In some embodiments, the disease is a solid cancer, hematopoietic cancer, hematological cancer, autoimmune disease, neurodegenerative disease, cardiovascular disease or pathogenic infection.

MRI imaging with a D-polymer-biomolecule conjugate may be used to qualitatively or quantitatively detect the targeting compound. A D-polymer-biomolecule conjugate imaging agent may be used as a biomarker, and the presence or absence of a positive signal in a subject may be indicative that, e.g., the subject would be responsive to a given therapy, e.g., a cancer therapy, or that the subject is responding or not to a therapy.

In some embodiments, the steps of this method can be repeated at determined intervals so that the location and/or size of the disease can be monitored as a function of time and/or treatment. In certain embodiments, the D-polymer-biomolecule conjugate can be used in a subject undergoing treatment (e.g., chemotherapy, etc.), to aid in visualizing response to the treatment. For example, the D-polymer-biomolecule conjugate is typically visualized and sized prior to treatment, and periodically (e.g., daily, weekly, monthly, intervals in between these, and the like) during treatment to monitor the progression or regression of the disease in the patient.

Accordingly, in certain aspects, provided is a method of monitoring the progress of a disease in a subject in need thereof, the method comprising administering to the subject a D-polymer-biomolecule conjugate which binds to a target molecule associated with the presence of the disease at a first time point and obtaining an image of at least a portion of the subject to determine the amount of diseased cells or tissue, and administering to the subject the D-polymer-biomolecule conjugate at one or more subsequent time points and obtaining an image of at least a portion of the subject at each subsequent time point (e.g., same portion as the first time point).

In certain embodiments, the size of a tumor can be monitored in a subject undergoing cancer therapy (e.g., chemotherapy, radiotherapy) and the extent of regression of the tumor can be monitored in real-time based on detection of D-polymer-biomolecule conjugate tumor targeting.

In some embodiments, the methods herein are used to evaluate the patient's response to therapy. In some embodiments, the methods are used to select or modify the dosage of therapeutic compounds. In some embodiments, the methods are used to monitor the uptake of the D-polymer-biomolecule conjugate in normal tissues to analyze toxicity or patient to patient variation. In some embodiments, the methods are used to monitor drug efficacy or to detect drug resistance.

In some embodiments, the radiolabeled compounds are administered to mammals, preferably humans, in a pharmaceutical composition, either alone or in combination with pharmaceutically acceptable carriers or diluents according to standard pharmaceutical practice. Such compositions can be administered orally or parenterally, including the intravenous, intramuscular, intraperitoneal, subcutaneous, rectal and topical routes of administration. In certain embodiments, administration is intravenous. In certain embodiments the radiolabeled compound is administered via intravenous injection within less than one hour of synthesis.

In some embodiments, the D-polymer-biomolecule conjugate provided herein is used in vitro as a screening tool to select compounds for use in treating tissues or cells. For example, in some embodiments, diseased cells are incubated with the D-polymer-biomolecule conjugate during or after exposure to one or more candidate drugs. The ability of the drug candidate to affect the disease can be imaged over time using the D-polymer-biomolecule conjugate.

For example, the integrity of biological activity of the D-polymer-biomolecule conjugate in vitro in terms of specific binding to the selected target molecule and uptake of the radiolabeled composition is assessed in a cell line expressing the target molecule. For binding and cell association assays, cells may be incubated at 4° C. or 37° C. for an appropriate time with the D-polymer-biomolecule conjugate. Nonspecific binding is determined by the addition of an excess of unlabeled targeting agent. The extent of specific binding is calculated by subtracting the nonspecific binding from the total binding. Uptake is expressed as a percentage of the total added dose of targeting agent to the cells per microgram of protein (% ID/$\mu$g cell protein).

In a related aspect, the present invention provides a diagnostic composition for in vivo or in vitro, which includes a D-polymer-biomolecule, and a pharmaceutically acceptable carrier.

X. Kits and Articles of Manufacture

Also provided are kits comprising a D-polymer-biomolecule-conjugate composition described herein, or precursor molecules for producing a D-polymer-biomolecule-conjugate and instructions for use. Kits typically include a packaged combination of reagents in predetermined amounts with instructions and a label indicating the intended use of the contents of the kit. The term label includes any writing, or recorded material supplied on or with the kit, or which otherwise accompanies the kit.

For example, in some embodiments, the kit contains the deuterated-polymer and the biomolecule, and instructions on linking the two prior to administration.

In certain embodiments, a kit comprises one or more reagents necessary for forming a D-polymer-FBS protein conjugate for use as an in vivo imaging agent, as further described herein. For example, a kit may comprise a first vial comprising FBS protein (e.g., anti-glypican-3 or anti-PDL Adnectin), and a second vial comprising D-polymer, e.g., D-PEG. A kit may comprise a first vial comprising an FBS protein, a second vial comprising a reactive linker and a third vial comprising D-polymer in water. The kits may further comprise vials, solutions and optionally additional reagents necessary for the manufacture of D-polymr-labeled FBS proteins.

In some embodiments, the kit can further contain at least one additional reagent (e.g., pharmaceutically acceptable carrier). In some embodiments, the kit includes the reaction precursors to be used to generate the labeled probe according to the methods disclosed herein. The components of the kit can be tailored to the particular biological condition to be monitored as described herein. The kit can further include appropriate buffers and reagents known in the art for administering various combinations of the components listed above to the host cell or host organism. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. Suitable containers include, for example, bottles, vials, syringes, and test tubes. The containers may be formed from a variety of materials such as glass or plastic. It may further include other materials desirable from a commercial and user standpoint, including other buffers, diluents, filters, needles, syringes, and package inserts with instructions for use.

INCORPORATION BY REFERENCE

All documents and references, including patent documents and websites, described herein are individually incorporated by reference to into this document to the same extent as if there were written in this document in full or in part.

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1

Deuterated imaging agents can be made by conjugating deuterated poly(ethylene glycol) ("D-PEG") to a targeting moiety that binds to a ligand at the organ or tissue of interest. The targeting moiety can an adnectin or the Fab unit of an antibody.

The D-PEG has a number average molecular weight (Mw) of between about 2 and about 100 kDa. It is known to conjugate a large PEG group (up to 40 kDa) to an adnectin (or another polypeptide) to extend its half-life. The use of a lower molecular weight D-PEG provides sufficient deuterium to generate a suitable D-MRI signal, but does not extend the half-life of the adnectin so much that its fast clearance from tissues or organs not of interest is precluded. In a D-PEG, preferably at least 90%, more preferably at least 95%, and even more preferably at least 98% of the hydrogens of the corresponding undeuterated PEG have been replaced by deuterium.

Suitable D-PEG is available from Polymer Source Inc., Dorval (Montreal), Canada, in a variety of Mns and having different terminal functional groups (OH, SH, $NH_2$) that can be used for conjugation to a targeting moiety:

HO—$(CD_2CD_2O)_n$H (Product numbers P4837-dPEO, Mn 2.7; P4836-dPEO, Mn 3.5; and P4927-dPEO, Mn 4.8).

$CD_3CD_2O$—$(CD_2CD_2O)_n$—H (Product number P3864A-dPEO, Mn 2.7).

$CH_3O$—$(CD_2CD_2O)_n$—H (Product numbers P5381-dPEO-$OCH_3$, Mn 2.2; P11450-dPEO-$OCH_3$, Mn 5).

$CD_3O$—$(CD_2CD_2O)_nCD_2CD_2NH_2$ (Product number P11448dPEG-OCH3NH2, Mn 5).

$CH_3O$—$(CD_2CD_2O)_nCD_2CD_2SH$ (Product number P5381A-dPEOOCH3SH, Mn 2)

Amine terminated D-PEG can be conjugated to a targeting moiety TM using the enzyme transglutaminase, which can form an amide bond between the D-PEG terminal amino group and the carboxamide group of the side chain of a glutamine in TM, as schematically shown below. An illustrative description on the use of transglutaminase to making conjugates, in the context of antibodies, is found in Jeger et al., Angew. Chem. Int. Ed. 2010, 49, 9995.

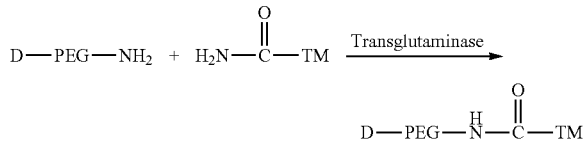

Hydroxyl or amine-terminated D-PEG can be reacted with 3-(2,5-dioxo-2,5-dihydro-1H-pyrrol-1-yl)propanoyl chloride (or its homolog 6-(2,5-dioxo-2,5-dihydro-1H-pyrrol-1-yl)hexanoyl chloride) to provide a maleimide-terminated D-PEG.

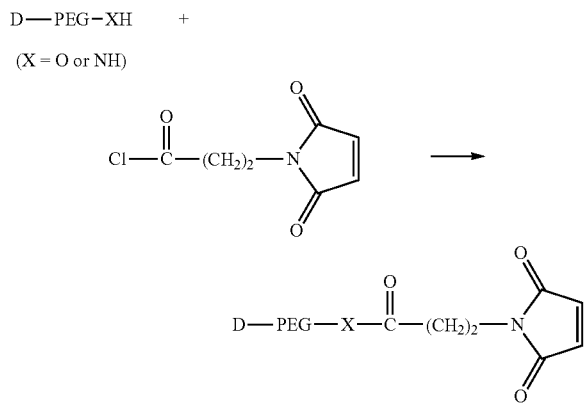

The maleimide-terminated D-PEG can then be conjugated to a targeting moiety TM by the Michael addition of a cysteine SH group to the maleimide, as shown following. (For an example of such maleimide-cysteine conjugation with an adnectin, see Lipovsek et al., WO 2017/053619 A1 (2017)).

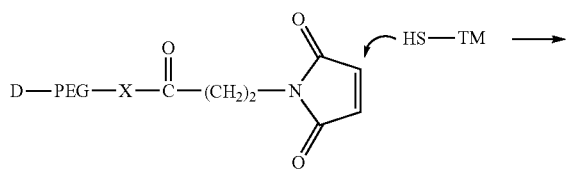

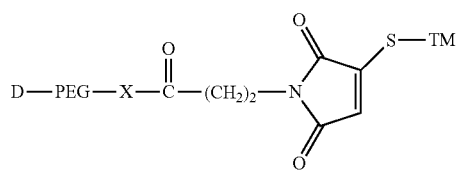

Where the TM lacks an available cysteine for conjugation, a "surrogate" cysteine can be created by reacting a lysine side chain amino group with 2-iminothiolane. The SH group of this "surrogate" cysteine can then be conjugated to a maleimide terminated D-PEG as described above.

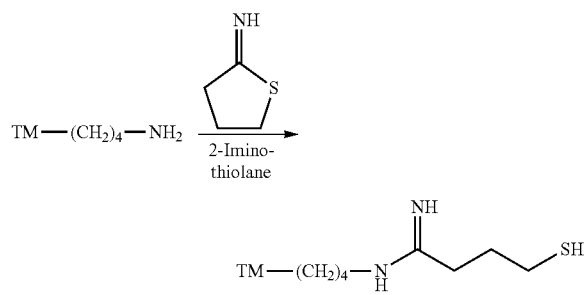

Where the D-PEG has a terminal sulfhydryl (SH) group, it can be conjugated to targeting moiety by first modifying the latter to introduce a maleimide group thereto and then performing a maleimide addition conjugation, as shown below:

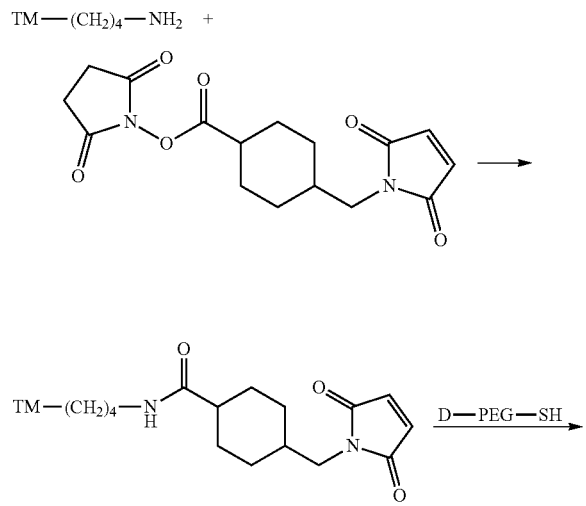

Example 2

A D-PEG-biomolecule conjugate can also be prepared as follows:

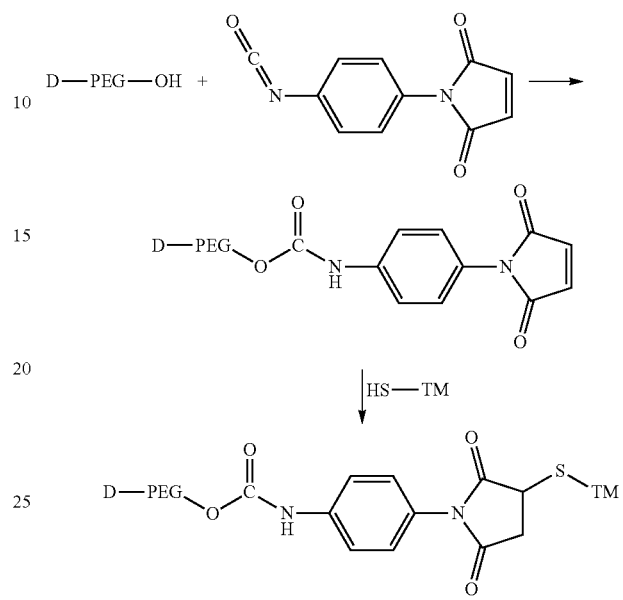

Example 3

Preparation of D-PEG-FBS Conjugate

C-PEG is conjugated to an FBS protein, which binds glypican-3, with the following amino acid sequence:

```
                                        (SEQ ID NO: 9)
VSDVPRDLEVVAATPTSLLISWSDDYHAHRYYRITYGETGGNSPVQEFTV

PGEHVTATISGLKPGVDYTITVYAVTYDGEKAATDWSISINYRTPC.
```

A deuterated PEG can be linked to the C-terminal cysteine according to the deuterated PEG manufacturer's instructions.

The amino acid sequences of other FBS proteins, binding to other target molecules, are provided in SEQ ID NO:2 through SEQ ID NO:8.

Example 4

$CH_3O—(CD_2CD_2O)_n—H$ is dissolved in solvent such as DMSO, DMF or toluene and PMPI ((N-[p-maleimidophenyl] isocyanate) is added. The desired maleimide-linked D-PEG product is then dissolved in appropriate buffer and exposed to a targeting moiety containing a sulfhydryl, such as a PD-L1 or GP3 FBS polypeptide, giving rise to the desired targeting imaging reagent.

Example 5

This examples and its accompanying figures demonstrate the use of deuterium MRI ($^2$H MRI) as a non-invasive means to trace the location of the drugs in a live body.

At 7T, the resonance frequency of deuterium ($^2$H) is 46 MHz, a large offset from that of the proton ($^1$H) which is 300

MHz. Deuterium is a promising nucleus for magnetic resonance in living systems because of its negligible background signals in biological tissue, as well as its greater stability compared to short-lived radio tracers in the localization and quantification of tissue uptake and deposition.

The demonstration was performed using deuterated poly (d4-ethylene glycol) methyl ether as the D-PEG: (Product #P11450-dPEO-OCH3, Polymer Source, Inc., Dorval (Montreal), Quebec, Canada). It has the structure shown below. Its Mw is 5,400, with about 84 monomer units per polymer (i.e., n~84). With four deuteriums per monomer, there are about 337 deuteriums per polymer. Thus a 1 mM solution of the D-PEG corresponds to 1 mM in deuterium.

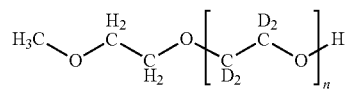

C57Bl/6 mice (n=3) were used, having a body weight of around 20-25 g. They dosed by a single oral administration of 2, 10, and 20 mg the D-PEG (in 0.3 mL water), corresponding to 80, 400 and 800 mg/kg body weight. Imaging timepoints were at ~30 min to 2 hours post-administration and at ~24 h post-dosing.

The mice were anesthetized with isoflurane (0.25-2° vol. in 2 liters/min air flow), and a core temperature of approximately 37.8° C. was maintained during MRI. The rectal temperature and respiration rates were monitored using MR-compatible systems (SA Instruments, Inc., Stony Brook, N.Y.).

MRI image acquisition was performed on a 7 Tesla/20 cm Bruker Biospec system using a 86-mm whole-body $^1$H RF coil (Bruker/Biospin, Billerica, Mass.) for proton MRI and a customized $^2$H surface coil for Deuterium MRI ($^2$H MRI). The mice were placed head-first in the prone position in the system with a respirator sensor and with the abdomen centered with respect to the center of the $^2$H surface coil. Anatomical $^1$H MRI scout images of coronal, sagittal and axial views were collected for slice planning, followed by the $^2$H MRI of mouse gut, and anatomical T2-weighted $^1$H MRI with fat suppression for co-registration of the $^2$H-MRI.

Three dimensional single-shot EPI (FID) was implemented at 7T system in house, using the following parameters: TR=100 ms; TE=6.9 ms; Flip_angle=90°; 200 averages; 3.2×3.2×3.2 cm$^3$ field of view, and 1×1×1 mm$^3$ isotropic resolution. Respiration gating was applied to minimize the respiration caused motion artifacts.

Figure 2A:
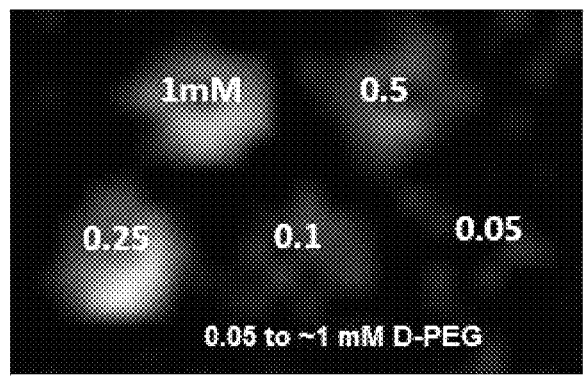
FIGS. 2A, 2B, and 2C relate to a phantom study for correlating the sensitivity of an $^2$H MRI coil for detecting the $^2$H signal.
Figure 2B:
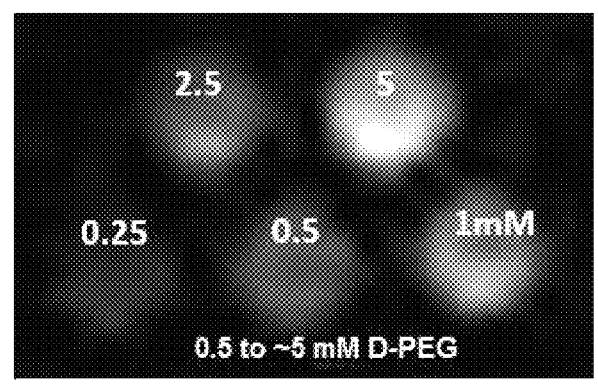
Figure 2C:
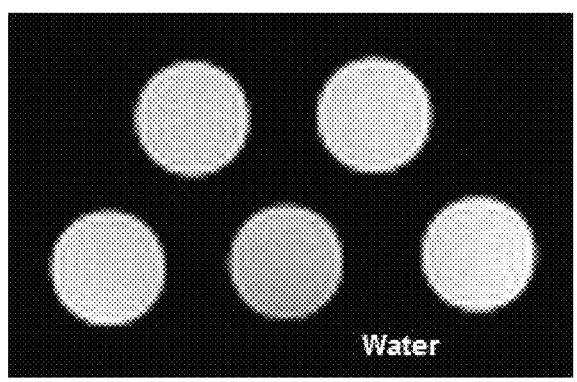
Figure 3:
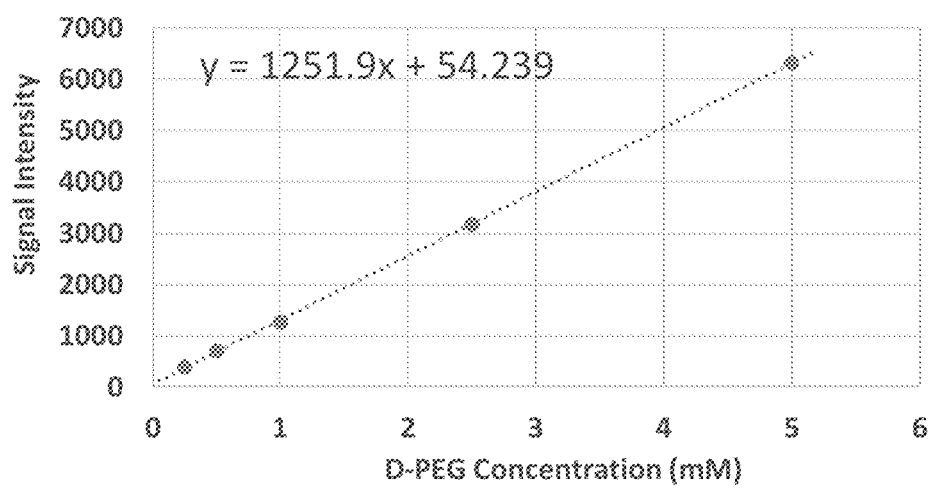
FIG. 3 is a graph showing the correlation between D-PEG concentration and signal intensity, from the study of FIGS. 2A-2C.

A phantom study was made to understand the dosing limitation of the D-PEG and the sensitivity of the $^2$H MRI coil to detect the $^2$H signal. Deuterium phantom tubes were made at various concentrations of D-PEG diluted in water solution (FIGS. 2A-2C). FIG. 2A is a $^2$H MRI of phantom tubes with D-PEG concentrations ranging from 0.05 to ~1 mM. FIG. 2B is a $^2$H MRI of phantom tubes with D-PEG concentrations ranging from 0.5 to ~5 mM. FIG. 2C is a $^1$H MRI (proton MRI) of the tubes. FIG. 3 shows the correlation between D-PEG concentration and signal intensity, with excellent linearity.

Figure 4:
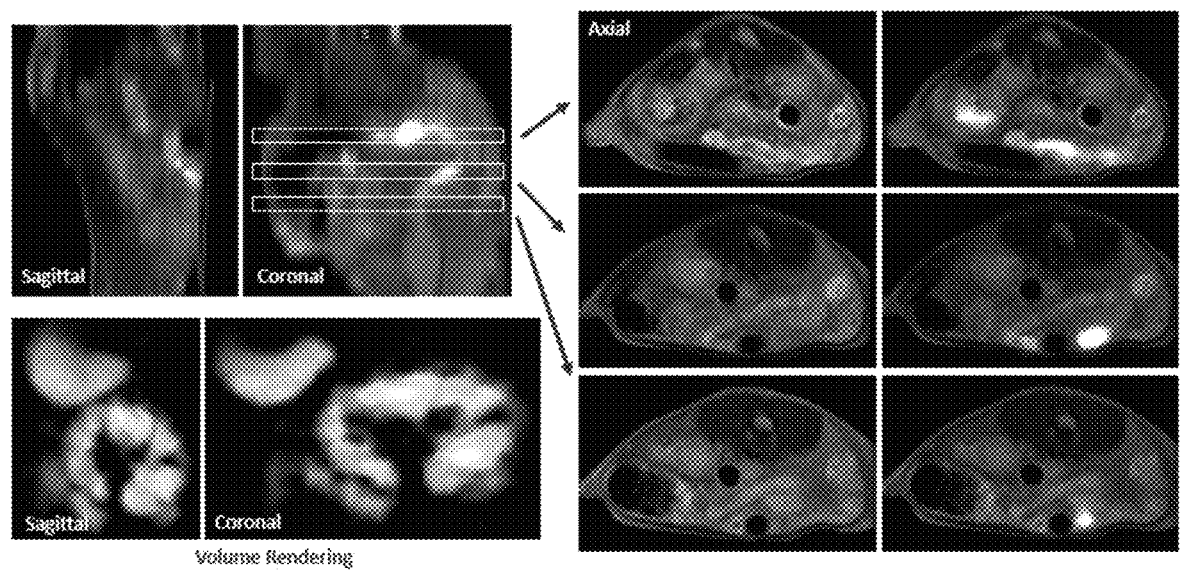
FIGS. 4, 5A, 5B, 6A and 6B are deuterium MRI images of the passage and excretion of D-PEG administered to mice through their gut.

FIG. 4 shows the D-MRI imaging of mouse gut 2 h post-administration (20 mg oral dosing), overlaid on a proton anatomical MRI, in sagittal, coronal, and axial views.

Figure 5A:
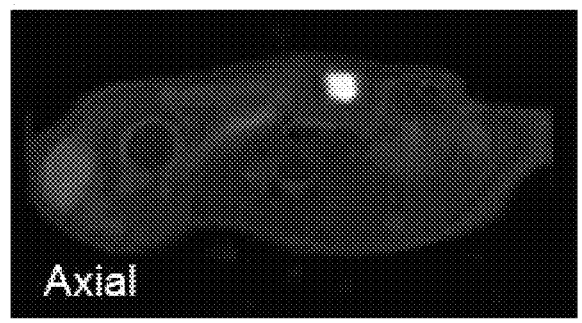
Figure 5B:
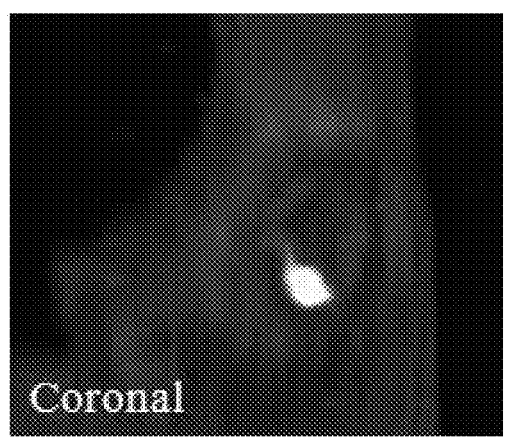

FIGS. 5A and 5B show the D MRI imaging of mouse gut 24 h post-administration (20 mg oral dosing) overlaid on a proton anatomical MRI image. The D-MRI signal was detected in the cecum region. Both axial and coronal views are presented.

Figure 6A:
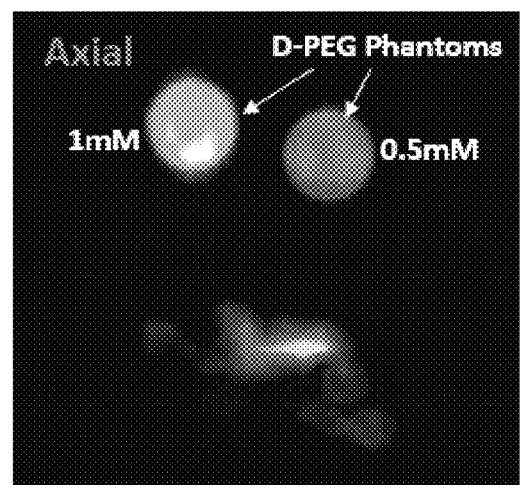
Figure 6B:
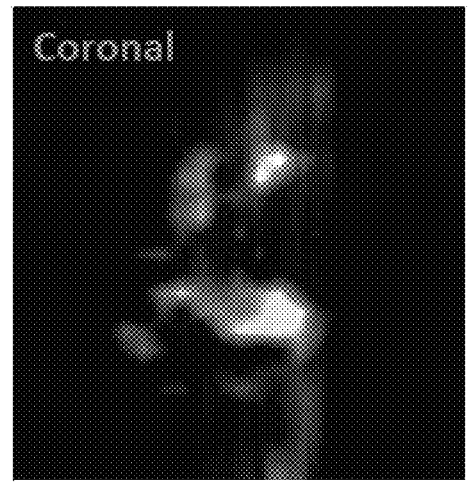

FIGS. 6A and 6B is a D-MRI image of rehydrated feces collected 24 h post-administration (20 mg dose), overlaid on the proton anatomical Mill, in both axial and coronal views.

EQUIVALENTS

Those skilled in the art will recognize, or be able to ascertain using no more than routine experimentation, many equivalents of the specific embodiments described herein. Such equivalents are intended to be encompassed by the following claims.

REFERENCES

Turecek P L, Bossard M J, Schoetens F, Ivens I A, PEGylation of Biopharmaceuticals: A Review of Chemistry and Nonclinical Safety Information of Approved Drugs, Journal of Pharmaceutical Sciences 2016; 105:460-475.

Swierczewska M, Lee K C, and Lee S, What is the future of PEGylated therapies? Expert Opin Emerg Drugs. 2015; 20(4):531-536.

Gant T G, Using Deuterium in Drug Discovery: Leaving the Label in the Drug. J. Med. Chem. 2014; 57 (9):3595-3611.

Pelham R W, Nix L C, Chavira R E, Cleveland M V B, and Stetson P., Clinical trial: single- and multiple-dose pharmacokinetics of polyethylene glycol (PEG-3350) in healthy young and elderly subjects. Aliment Pharmacol Ther. 2008; 28(2):256-65.

TABLE 1

SUMMARY OF SEQUENCES

| SEQ ID | Description | Sequence |
|---|---|---|
| 1 | WT $^{10}$Fn3 domain | VSDVPRDLEVVAATPTSLLISWDAPAVTVRYYRI TYGETGGNSPVQEFTVPGSKSTATISGLKPGVDY TITVYAVTGRGDSPASSKPISINYRT |
| 2 | PDL-1 FBS (A02) | VSDVPRDLEVVAATPTSLLISWSYDGPIDRYYRI TYGETGGNSPVQEFTVPPDQKTATISGLKPGVDY TITVYAVRLEEAHYNREFPISINYRT |
| 3 | PDL-1 FBS (E01) | VSDVPRDLEVVAATPTSLLISWRAQLSPSFYYRI TYGETGGNSPVQEFTVPNDVMTATISGLKPGVDY TITVYAVTTHGVYFYSPISINYRT |
| 4 | PDL-1 FBS (ATI-964) | VSDVPRDLEVVAATPTSLLISWSYDGSIERYYRI TYGETGGNSPVQEFTVPPDQKTATISGLKPGVDY TITVYAVRLEEAHYYRESPISINYRT |
| 5 | PDL-1 FBS (ATI-965) | VSDVPRDLEVVAATPTSLLISWTAYDSVDKYYRI TYGETGGNSPVQEFTVGPRHHTATISGLKPGVDY TITVYAVYHTEPGYHAHMPISINYRT |
| 6 | PDL-1 FBS (ATI-966) | VSDVPRDLEVVAATPTSLLISWHRFSSIMAYYRI TYGETGGNSPVQEFTVAGSVNTATISGLKPGVDY TITVYAVTIHNVSFPISINYRT |
| 7 | PDL-1 FBS (ATI-967) | VSDVPRDLEVVAATPTSLLISWQGQLSPSFYYRI TYGETGGNSPVQEFTVPVASGTATISGLKPGVDY TITVYAVTSHGIYFYAPISINYRT |

TABLE 1-continued

SUMMARY OF SEQUENCES

| SEQ ID | Description | Sequence |
|---|---|---|
| 8 | PDL-1 FBS (ATI-968) | VSDVPRDLEVVAATPTSLLISWIAPFYNVIYYRI TYGETGGNSPVQEFTVPGTGYTATISGLKPGVDY TITVYAVTDGASIASYAFPPISINYRT |
| 9 | Glypican-3 FBS sequence | VSDVPRDLEVVAATPTSLLISWSDDYHAHRYYRI TYGETGGNSPVQEFTVPGEHVTATISGLKPGVDY TITVYAVTYDGEKAATDWSISINYRTPC |

What is claimed is:

1. A method of obtaining an image of a D-polymer-biomolecule conjugate in a subject, the method comprising:
   (a) administering the D-polymer-biomolecule conjugate to the subject; and
   (b) imaging in vivo the distribution of the D-polymer-biomolecule conjugate by magnetic resonance imaging (MRI),
   wherein the D-polymer is D-PEG that is 50-100% deuterated.

2. A method of diagnosing the presence of a disease in a subject, the method comprising:
   (a) administering to a subject in need thereof a D-polymer-biomolecule conjugate, which conjugate binds to a target molecule associated with the presence of the disease; and
   (b) obtaining a magnetic resonance image of at least a portion of the subject to detect the presence or absence of the D-polymer-biomolecule conjugate;
   wherein the presence and location of the D-polymer-biomolecule conjugate above background is indicative of the presence and location of the disease, and
   wherein the D-polymer is D-PEG that is 50-100% deuterated.

3. The method of claim 2, wherein the disease is selected from the group consisting of solid cancers, hematopoietic cancers, hematological cancers, autoimmune disease, neurodegenerative disease cardiovascular disease, and pathogenic infection.

4. A method of monitoring the progress of a disease in a subject, the method comprising:
   (a) administering to the subject a D-polymer-biomolecule conjugate, which conjugate binds to a target molecule associated with the presence of the disease at a first time point and obtaining an image of at least a portion of the subject to determine the amount of the diseased cells or tissue; and
   (b) administering to the subject the D-polymer-biomolecule conjugate at one or more subsequent time points and obtaining an image of at least a portion of the subject at each time point;
   wherein the dimension and location of the diseased cells or tissue at each time point is indicative of the progress of the disease, and
   wherein the D-polymer is D-PEG that is 50-100% deuterated.

5. The method of claim 4, wherein the disease is selected from the group consisting of solid cancers, hematopoietic cancers, hematological cancers, autoimmune disease, neurodegenerative disease cardiovascular disease, and pathogenic infection.

6. A method of determining the distribution of a deuterated molecule in a subject, the method comprising:
   (a) orally administering the deuterated molecule to the subject; and
   (b) imaging in vivo the distribution of the deuterated molecule by magnetic resonance imaging (MRI),
   wherein the D-polymer is D-PEG that is 50-100% deuterated.

7. The method of claim 1 wherein the D-PEG is at least about 90% deuterated.

8. The method of claim 2 wherein the D-PEG is at least about 90% deuterated.

9. The method of claim 4 wherein the D-PEG is at least about 90% deuterated.

10. The method of claim 6 wherein the D-PEG is at least about 90% deuterated.

11. The method of claim 1 wherein the biomolecule is an antibody or antigen-binding fragment thereof.

12. The method of claim 2 wherein the biomolecule is an antibody or antigen-binding fragment thereof.

13. The method of claim 4 wherein the biomolecule is an antibody or antigen-binding fragment thereof.

14. The method of claim 6 wherein the biomolecule is an antibody or antigen-binding fragment thereof.

15. The method of claim 7 wherein the biomolecule is an antibody or antigen-binding fragment thereof.

16. The method of claim 8 wherein the biomolecule is an antibody or antigen-binding fragment thereof.

17. The method of claim 9 wherein the biomolecule is an antibody or antigen-binding fragment thereof.

18. The method of claim 10 wherein the biomolecule is an antibody or antigen-binding fragment thereof.

\* \* \* \* \*

UNITED STATES PATENT AND TRADEMARK OFFICE
CERTIFICATE OF CORRECTION

| | | |
|---|---|---|
| PATENT NO. | : 11,623,013 B2 | Page 1 of 1 |
| APPLICATION NO. | : 17/093941 | |
| DATED | : April 11, 2023 | |
| INVENTOR(S) | : Smith et al. | |

It is certified that error appears in the above-identified patent and that said Letters Patent is hereby corrected as shown below:

On the Title Page

Item (56), Column 2, Line 12, under OTHER PUBLICATIONS, Zhang et al. . . .:
Delete "Proteolystic" and insert -- Proteolytic --.

In the Claims

Claim 3, Column 41, Line 58:
Delete "disease cardiovascular" and insert -- disease, cardiovascular --.

Claim 5, Column 42, Line 42:
Delete "disease cardiovascular" and insert -- disease, cardiovascular --.

Signed and Sealed this
Twenty-seventh Day of June, 2023

Katherine Kelly Vidal
*Director of the United States Patent and Trademark Office*